United States Patent
Bacon et al.

(10) Patent No.: US 9,486,510 B2
(45) Date of Patent: *Nov. 8, 2016

(54) METHOD TO ENHANCE AN IMMUNE RESPONSE OF NUCLEIC ACID VACCINATION

(71) Applicant: Lipoxen Technologies Limited, London (GB)

(72) Inventors: Andrew David Bacon, London (GB); Peter Laing, London (GB); Gregory Gregoriadis, London (GB); Wilson Romero Caparros-Wanderley, London (GB)

(73) Assignee: LIPOXEN TECHNOLOGIES LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/447,556

(22) Filed: Jul. 30, 2014

(65) Prior Publication Data

US 2014/0341980 A1 Nov. 20, 2014

Related U.S. Application Data

(60) Division of application No. 13/292,778, filed on Nov. 9, 2011, now Pat. No. 8,828,405, which is a continuation of application No. 12/566,587, filed on Sep. 24, 2009, now Pat. No. 8,075,896, which is a continuation of application No. 10/520,169, filed as application No. PCT/GB03/02935 on Jul. 7, 2003, now Pat. No. 7,604,803.

(30) Foreign Application Priority Data

Jul. 5, 2002 (EP) ..................... 02254733

(51) Int. Cl.
*A61K 9/48* (2006.01)
*A61K 39/00* (2006.01)
*A61K 39/12* (2006.01)
*A61K 39/02* (2006.01)
*C07H 21/04* (2006.01)
*A61K 39/145* (2006.01)
*C12N 7/00* (2006.01)
*A61K 39/29* (2006.01)
*A61K 39/39* (2006.01)

(52) U.S. Cl.
CPC ............... *A61K 39/00* (2013.01); *A61K 39/12* (2013.01); *A61K 39/145* (2013.01); *A61K 39/292* (2013.01); *A61K 39/39* (2013.01); *C12N 7/00* (2013.01); *A61K 2039/53* (2013.01); *A61K 2039/55555* (2013.01); *A61K 2039/70* (2013.01); *C07H 21/04* (2013.01); *C12N 2730/10134* (2013.01); *C12N 2760/16134* (2013.01)

(58) Field of Classification Search
CPC ............... A61K 39/00; A61K 39/145; A61K 2039/53; A61K 2039/55555; C07H 21/04; C12N 7/00; C12N 2760/16134
USPC ............ 424/450, 184.1, 204.1, 234.1, 277.1; 536/23.5, 23.7
See application file for complete search history.

(56) References Cited

U.S. PATENT DOCUMENTS

| 5,459,127 | A | 10/1995 | Feigner et al. |
| 6,030,619 | A | 2/2000 | Granoff et al. |
| 6,166,177 | A | 12/2000 | Probst et al. |
| 7,008,791 | B1 | 3/2006 | Gregoriadis et al. |
| 7,285,289 | B2 | 10/2007 | Nagy et al. |
| 7,381,421 | B2 | 6/2008 | Gregoriadis |
| 8,075,896 | B2* | 12/2011 | Bacon .............. A61K 39/00 424/184.1 |
| 8,828,405 | B2* | 9/2014 | Bacon .............. A61K 39/00 424/184.1 |

FOREIGN PATENT DOCUMENTS

| WO | 9728818 | 8/1997 |
| WO | 9810748 | 3/1998 |
| WO | 9930733 | 6/1999 |
| WO | 0141739 | 6/2001 |
| WO | 0156548 | 8/2001 |

OTHER PUBLICATIONS

Alvarez-Lajonchere et al., "Additives and protein-DNA combinations modulate the humoral immune response elicited by a hepatitis C virus core-encoding plasmid in mice.", Mem. Inst Oswaldo Cruz, Rio de Janeiro (2002) 97(1):95-99.
Chen et al., "Genetic Immunization of Mice with Plasmids Containing Hepatitis C Virus Core Protein-Encoding DNA", Vaccine Res 1995, 4, 135-144.
Cox RA., "Correlation of the rate of protein synthesis and the third power of the RNA: protein ratio in *Escherichia coli* and *Mycobacterium tuberculosis*.", Microbiology. Mar. 2003; 149 (Pt 3):729-37.
Fazel-Madjlessi J., et. al. "Analysis of fermentation processes using flow microfluorometry: Single-parameter observations of batch bacterial growth.", Biotechnol Bioeng. Sep. 5, 2002;79(5):532-8.
Gregoriadis et al., "High yield incorporation of plasmid DNA within liposomes: effect on DNA integrity and transfection efficiency", Journal of Drug Targeting (1996) 3:469-475.

(Continued)

*Primary Examiner* — Shin Lin Chen
(74) *Attorney, Agent, or Firm* — One3 IP Management, P.C.; Annette S. Parent; Dean G. Stathakis

(57) ABSTRACT

A composition comprising liposomes associated with a nucleic acid operatively encoding an antigenic protein and with an assistor protein, wherein the assistor protein shares at least one epitope with the antigenic protein, and wherein the nucleic acid and said assistor protein are associated with the same liposomes is described. The composition provides an improved immune response compared to mixtures of liposomes some of which are associated with the nucleic acid and some of which are associated with the assistor protein.

22 Claims, 8 Drawing Sheets

(56) References Cited

OTHER PUBLICATIONS

Gregoriadis et al., "Vaccine Entrapment in Liposomes", Methods: A Companion to Methods in Enzymology, Academic Press Inc., vol. 19, No. 1, Sep. 1999, pp. 156-162.
Gursel et al., "Immunoadjuvant action of plasmid DNA in liposomes.", Vaccine (1999) 17:1376-1383.
Kato et al., 1991, The Journal of Biological Chemistry, vol. 266, No. 6, pp. 3361-3364.
Kirby et al., "Dehydration-Rehydration Vesicles: A Simple Method for High Yield Drug Entrapment in Liposomes", Biotechnology, Nov. 1984, pp. 465-472.
Klinman et al., "CpG motifs as immune adjuvants.", Vaccine (1999) 17:19-25.
Lanzavecchia, "Antigen-specific interaction between T and B cells.", Nature (1985) 314:537-539.
McCluskie et al., "Route and method of delivery of DNA vaccine influence immune responses in mice and non-human primates.", Molecular Medicine (1999) 5:287-300.
Pancer et al., Ann. R. Immunology (2006) doi:10.1146/annurev.immunol.24.021605.090542.
Potter et al., "Obstacles to successful antiretroviral treatment of HIV-1 infection: problems & perspectives.", Indian J. Med. Res. (2004) 119:217-237.
Senior et al., "Dehydration-rehydration vesicle methodology facilitates a novel approach to antibody binding to liposomes.", Biochimica et Biophysica Acta (1989) 1003:58-62.
Shahum et al., 1995, Int. J. Immunopharmac., vol. 17, No. 1, pp. 9-20.
Titti et al., "Problems and emerging approaches in HIV/AIDS vaccine development.", Expert Opin. Emerging Drugs (2007) 12:23-48.
Zadi et al.,"A Novel Method for High-Yield Entrapment of Solutes into Small Liposomes.", Journal of Liposome Research (2000) 10:73-80.

* cited by examiner

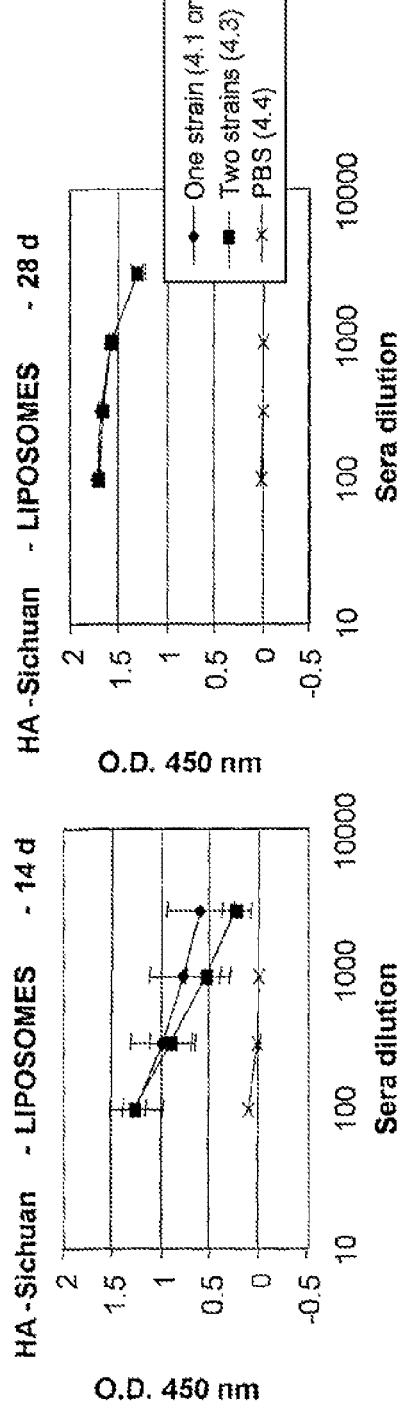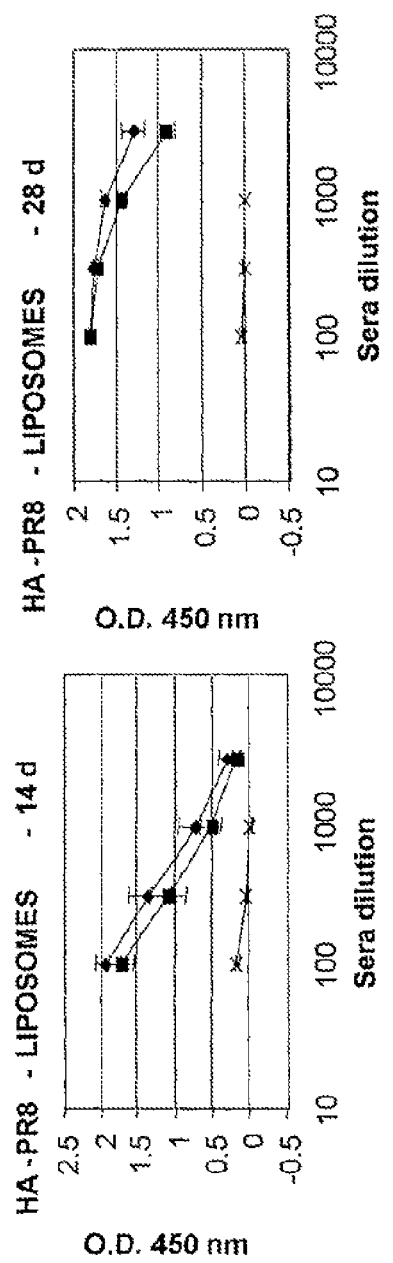

METHOD TO ENHANCE AN IMMUNE RESPONSE OF NUCLEIC ACID VACCINATION

CROSS-REFERENCE TO RELATED APPLICATIONS

This application is a divisional of U.S. application Ser. No. 13/292,778 filed 9 Nov. 2011, which is a continuation of U.S. application Ser. No. 12/566,587 filed 24 Sep. 2009, now U.S. Pat. No. 8,075,896, issued on 13 Dec. 2011 which is a continuation of U.S. application Ser. No. 10/520,169 filed 27 Apr. 2005, now U.S. Pat. No. 7,604,803, issued 20 Oct. 2009, which is a national stage application of PCT/GB03/02935 filed 7 Jul. 2003, which claims priority to European Patent Application 02254733.5 filed 5 Jul. 2002. The contents of the above patent applications and patents are incorporated by reference herein in their entirety.

TECHNICAL FIELD

The present invention relates to compositions for the co-delivery of nucleic acid and protein. Co-delivery means delivery to the same cell. The compositions are useful for generating an immune response. In particular, the nucleic acid operatively encodes an antigenic protein or protein thereof the sequence of which is homologous, preferably identical, to that of an 'assistor protein' which forms part of the compositions.

BACKGROUND

Protein antigens from pathogens have long been used in vaccines, designed to elicit neutralising antibody or cell-mediated immune responses in the recipient, specific for the antigen. Proteins however are generally not good at eliciting certain types of cell-mediated immune response, particularly the generation of effector T-cells (including cytotoxic T-cells), which are a desirable component of the response for a great many vaccines (particularly those directed against intracellular pathogens or cancer antigens). Latterly, vaccines have been developed based on naked DNA, usually plasmid DNA produced from *E. coli* but containing appropriate promoter sequences for expression in mammalian cells. These latter vaccines have transpired to be good at generating ceil mediated immunity (involving effector T-cells, such as interferon-.gamma. secreting antigen-specific T-cells and antigen-specific cytotoxic T-cells), but are poor at generating antibodies against the encoded and expressed antigen. Antibodies are an important component of the protective immune response for a great many pathogens—particularly bacteria and certain viruses such as the influenza viruses. Various remedies have been proposed and explored to rectify the deficiencies of DNA-based vaccines as described below.

Liposomal formulation has been used to enhance the immunogenicity of vaccine antigens, in the protein form, for many years. Liposomal formulation has also been applied in recent years to the formulation of DNA for vaccine purposes. These are studies which have described the co-formulation of plasmid DNA with proteins using liposomes. However, these studies of liposomal co-formulation of DNA with protein have generally used plasmids encoding immunostimulatory cytokines or other biologically active proteins—other than antigen itself. To incorporate the protein form of the antigen itself into a vaccine composition containing a nucleic acid which is designed to express the protein in vivo would seem unnecessary. We are aware of only one publication which has used protein antigen as an additive in the formulation alongside DNA (Alvarez-Lajonchere, L., et al., Mem Inst Oswaldo Cruz, Rio de Janiero, 97(1):95-99. January 2002). Unlike the present invention, no enhancement of antibody response was seen by these authors in co-formulations of the antigen-encoding DNA and its cognate protein compared to immunizations with the protein alone. The formulations used by Alvarez-Lajonchere, et al., comprised mixtures of the active nucleic acid (a plasmid encoding the core antigen of hepatitis-C virus) plus irrelevant carrier DNA and polyethylene glycol, and the protein. Following injection, the protein and the active DNA (which were not physically associated in the mixture) would diffuse independently and reach antigen presenting cells separately. The negative findings of Alvarez-Lajonchere would suggest, to a person skilled in the art, that formulation of protein with its cognate DNA was not a promising way to achieve improved immune responses, at least not improved antibody responses.

In WO-A-9930733 the immune response to a nucleic acid vaccine is proposed to be enhanced by simultaneous administration of a cognate protein. The two components do not need to be administered in the same composition. Both must merely be administered during the induction phase of the immune response with the protein preferably being masked or held back until after the nucleic acid has printed the immune system. In some examples of vaccine comprised naked DNA and naked protein antigen in physical admixture. In others the protein antigen was formulated for delayed release in a biodegradable polymer-alum formulation admixed with naked DNA.

In WO-A-9728817 vaccines are intended to deliver nucleic acid and protein antigen into antigen presenting cells. The nucleic acid may express the same protein as the protein antigen. The nucleic acid and protein are complexed, e.g., by covalent conjugation. The complex may be formulated as a synthetic virus-like particle. It is also suggested that liposomal systems may be used but there are no examples as to how both protein an dnucleic acid should be incorporated into such systems, nor does the specification include any quantitative results for in vivo tests but predicts results which may not in practice occur, especially class II responses.

It is known that non-coding plasmid DNA has an immuno-adjuvant action when coentrapped with peptides in liposomal vesicles (Gursel, M., et al., *Vaccine* (1999) 17:1376-1383) and that DNA with CpG motifs has an immuno adjuvant effect on naked DNA and peptide vaccines (Klinman, D. M. et al., *Vaccine* (1999) 17:19-25).

BRIEF SUMMARY

In the present invention however, we imagined that if we contrived to physically associate nucleic acid, such as DNA, together with its cognate protein and entrap them, that the two entities would arrive at antigen-presenting cells together, resulting in the processing and presentation of the acquired protein form of the antigen, together with the expression of the DNA-encoded form of the antigenic protein in the same cell. Since antigen processing of expressed proteins occurs by a different pathway and with kinetics that are somewhat different to that for acquired proteins, we imagined that such co-delivery of DNA associated with its cognate protein would provide an opportunity for an additive or synergistic effect of these two modes of antigen presentation, and an improved immune response.

Now we have tested this new hypothesis with vesicular formulations of DNA and its cognate protein which provide for the association of the DNA and protein. Unlike Alvarez-Lajonchere, et al., we have found that special vaccine compositions are possible, of DNA associated (via liposomes) with its cognate protein, called an 'assistor protein', wherein enhanced antibody responses are observed following immunisation (compared to immunisation with protein alone, or with DNA alone). We find that if the DNA and the protein are formulated in separate particles, and the particles are mixed, then we see no enhancement of antibody production. These observations are consistent with our theory of co-delivery of DNA and the assistor protein to the same antigen presenting cell, although we acknowledge that there may be other theoretical explanations that can not be excluded at the time.

This invention provides a composition for the co-delivery to a cell of a nucleic acid and an assistor protein comprising vesicles formed of amphiphilic components, wherein the nucleic acid operatively encodes an antigenic protein or portion thereof which shares at least one epitope with the assistor protein, the composition comprising said nucleic acid and said assistor protein being associated with the same vesicles as one another.

The term assistor protein refers to whole proteins or fragments of proteins, proteins of a single type or proteins of different types.

The antigenic protein encoded by the nucleic acid is generally the protein of interest, i.e., the target antigen against which a beneficial immune response is desired in a subject. The assistor protein is generally identical to the expressed form of nucleic-acid encoded antigenic protein, i.e., the conjugate protein of the nucleic acid. The antigenic protein and/or the assistor protein may each (severally) comprise the full sequence of the naturally occurring protein from the relevant source. Preferably the nucleic acid encodes the entire naturally occurring protein antigen. Alternatively, the nucleic acid may encode a portion only of the natural protein, including at least one of the epitopes of the assistor protein. In one favourable embodiment of the invention, said epitope is a B-cell epitope which is exposed on the surface of an infectious agent in its naturally occurring form. The nucleic acid may encode a portion only of the natural protein, including at least one of the epitopes of the naturally occurring agent. The agent is, for instance, a microorganism, for instance a bacterium, or a yeast or a virus. Similarly, the assistor protein should contain epitopes derived from the respective source which are (in one embodiment) surface accessible when the source is in its natural environment. Alternatively and usefully, both antigenic protein and assistor protein share epitope(s) with a secreted toxic product of a pathogen, such as tetanus toxin, appropriate to neutralisation of such toxin. Likewise, both antigenic protein and assistor protein may share epitope(s) with each other, which is/are also shared with a secreted product of a pathogen other than a toxin, such as the interleukin-10 analogue encoded by Epstein-Barr virus and secreted by cells infected with the Epstein-Barr virus.

BRIEF DESCRIPTION OF FIGURES

FIG. 9a shows the antibody responses (Sera ELISA) to the anti influenza HA-Sichuan at day 14; FIG. 9b shows the antibody responses (Sera ELISA) to the anti influenza HA-Sichuan at day 28; FIG. 9c shows the antibody responses (Sera ELISA) to the anti influenza HA-Puerto Rico 8 (PR8) at day 14; FIG. 9d shows the antibody responses (Sera ELISA) to the anti influenza HA-Puerto Rico 8 (PR8) at day 28. The legend for the symbols used in FIGS. 9A, 9B, 9C and 9D is shown in FIG. 9B.

DETAILED DESCRIPTION

Figure 1:
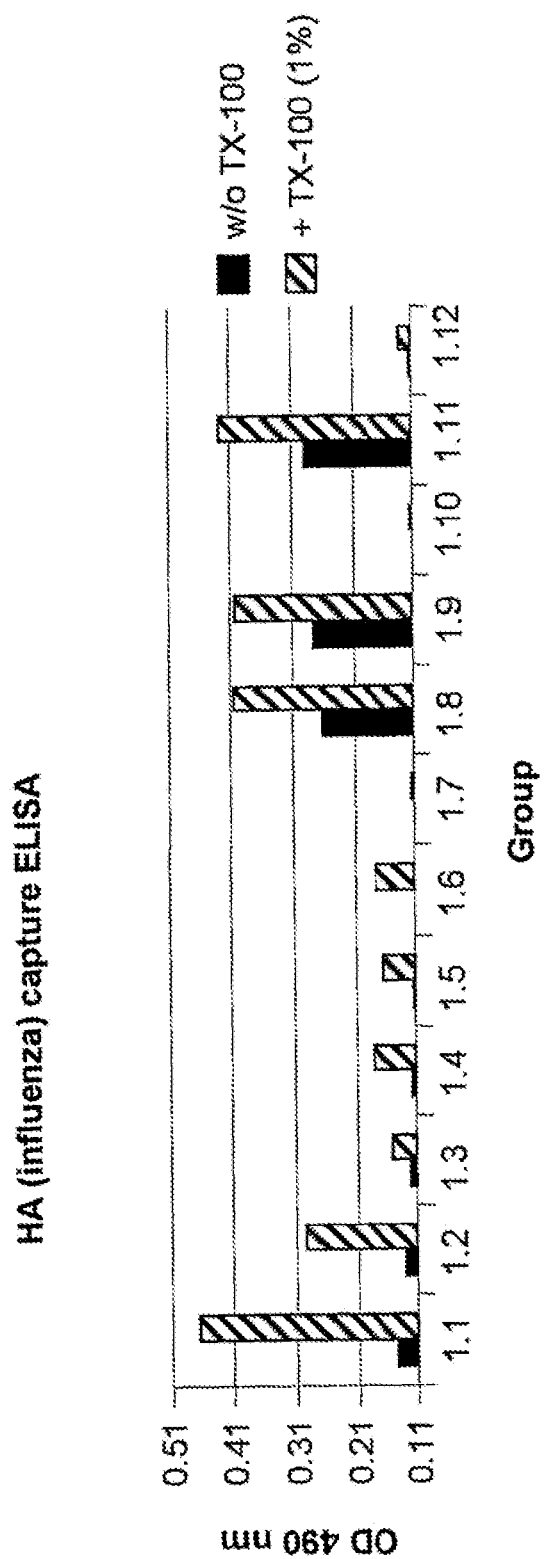
FIG. 1 shows an assessment of the formulations (Table 2) for HA antigenicity by capture ELISA.

We have formulated two related theories to explain the improved performance of the new compositions which are not mutually exclusive. We refer to these theories as the general and specific theories (as described below).

The General Theory

The general theory states that the enhanced performance of appropriately co-formulated material (wherein both DNA and its cognate protein are associated with a single vesicle, such that vesicles in a population have both DNA and protein) is due to the acquisition of both nucleic acid and its cognate protein (the assistor protein) by the same antigen presenting cell (be it a classical antigen presenting cell such as a macrophage or dendritic cell, or a B-cell, be it antigen specific or non-antigen specific). The co-delivery of the DNA and its cognate protein to the same cell allows a synergistic interaction in the ensuing immune response which would not be possible if the DNA were to be acquired by one antigen presenting cell, and the protein by another. (Previously described compositions do not provide for or recognize the importance of co-delivery of DNA and its cognate protein to the same antigen presenting cell).

The Specific Theory

The specific theory states that the enhanced performance of appropriately co-formulated material (wherein both DNA and its cognate protein are associated with a single vesicle, such that vesicles in a population have both DNA and protein) involves the targeting (by antigen in the protein form, exposed at the surface of the particle) of the vesicle to antigen-specific B-cells, thereby selectively delivering both DNA and its cognate protein in a targeted manner to the same antigen-specific B-cell. Since the antigen-specific B-cells will ordinarily proliferate in the course of an immune response, these proliferating cells are likely to form better targets for transduction by the nucleic acid also present in the particle than would non-proliferating cells. As in the case of the general theory above, the co-delivery of the DNA and its cognate protein to the same cell allows a synergistic interaction in the ensuing immune response which would not be possible if the DNA were to be acquired by one antigen presenting cell (in the case an antigen-specific B-cell), and the protein by another. In the specific form of the theory, the particles are captured by the antigen-specific receptors (i.e., surface antibodies) of B-cells, and the nucleic acid plus its cognate protein (the assistor protein) are both taken up by individual antigen-specific B-cells.

The efficiency of nucleic-acid-based immunisation is limited by the low transduction efficiency that is achieved in vivo with naked formulations of the antigen-encoding nucleic acid (e.g., naked DNA), such that few cells take up and express the nucleic acid of interest. In the exemplification of the present invention we have used vesicular, primarily liposomal, compositions to achieve protection of the DNA from nucleases in vivo, and to allow co-formulation of the DNA and its cognate protein (the assistor protein) in the same particle, although it should be clear to the reader that other vesicular compositions might be used to achieve association of DNA and its cognate protein to achieve the necessary properties of co-delivery herein defined.

In a particular preferred composition according to the invention, the vesicles comprise liposomes formed from liposome forming materials, i.e., formed of lipid bilayers. The vesicles may alternatively be mono-layer. Liposomes may comprise synthetic amphiphile components, such as surfactant type molecules. Non-ionic vesicles of this type are often known as niosomes. The vesicles may not comprise phospholipids, but preferably are based substantially on phospholipids.

In the course of our own studies using liposomal compositions we endeavored to obtain efficient co-entrapment and/or association of protein and DNA in the same liposomal particles. We found that the liposomal compositions we have developed for packaging and protection of DNA against nucleases and for DNA immunisation (as described in our earlier case WO-A-9010748) are also very efficient at co-packaging protein at the same time. Surprisingly, under the conditions herein defined for formulation of the liposomes, the DNA and protein do not compete with one another for association or containment in the liposomal particle. Moreover, they are also capable of displaying significant quantities of the assistor protein in antigenically active form at the surface of the liposomal particle. We believe that the surface-localised protein antigen of our new composition (the assistor protein) may be capable of targeting liposomes, or liposome fragments generated in vivo from breakdown of these structures, to antigen-specific B-cells.

Although liposomally formulated DNA can be targeted to receptors on antigen presenting cells, e.g., by placing ligands for cellular receptors of antigen presenting cells on the surface of liposomes (e.g., mannosyl moieties or complement proteins such as C3d), antigen itself has not previously been used as a targeting device in nucleic acid based vaccines.

The new compositions allow for the simultaneous presentation by antigen-presenting cells of both the acquired protein form of the antigen (the assistor protein), plus the expressed form of the protein from its cognate nucleic acid. Such compositions allows a novel prime-boost effect whereby the differing kinetics of presentation of the expressed antigenic protein and the assistor protein (having maxima at different times) provide for a longer-lasting and 'double it' exposure of the relevant immune cells to the antigen. Unlike other prime-boost phenomena in the nucleic acid vaccine field, the novel compositions provide prime and boost functions with a single dose.

Another advantageous feature of the new compositions relates to the differing modes of antigen presentation of the two forms (the added form and the in vivo expressed forms of the protein). Since acquired and expressed protein are presented by two distinct pathways in antigen presenting cells (the former resulting in peptide presentation via class-II MHC, the latter via class-I MHC) the new invention provides for a more broadly based immune response involving the stimulation of T-helper cells (class-II restricted), class-II restricted effector T-cells and cytotoxic T-cells (class-I restricted). The cellular microenvironment created by the new compositions (wherein both class-II and class-I presentation are occurring at the same antigen-presenting cell surface at the same time) allows for interactions among the differing T-cell types that engage the antigen-presenting cell. Since both T-cell types (class-I and class-II restricted) can be stimulated during interaction with the same antigen presenting cell, and by interactions with each other while simultaneously present at the antigen-presenting cell surface, the new formulation has several theoretical advantages over previously described methods and compositions for nucleic acid immunisation. Here we describe that the theoretical advantages are confirmed in practice at the level of antibody responses to the antigen. We predict however that further advantages will be found for the new formulation strategy in stimulating cell-mediacted immunity (including T-helper cell responses and effector T-cell responses including cytotoxic T-cells). Since antibody responses to protein antigens are highly T-cell dependent, the data presented in this application on antibody production strongly suggest that the new compositions are effective at stimulating (at least) T-helper cell (MHC class-II restricted) responses. The fact that the new formulation strategy provides for simultaneous stimulation of class-II restricted helper and class-I restricted cytotoxic cells on the same antigen presenting cell, also suggests that the strategy will be effective in the stimulation of cytotoxic T-cell responses. Thus, the assistor protein will provide additional help for cytotoxic T-cell responses, i.e., it will increase the concentration and/or duration of expression of MHC class-II restricted peptide epitopes of the antigen recognized by T-helper cells at the surface of the antigen-presenting cell, increasing the opportunity for T-cell help of cytotoxic T-cell responses to the expressed form of the protein antigen presented via the class-I MHC pathway.

An immune response requires co-operation between different cells of the immune system, namely antigen presenting cells (such as macrophages and dendritic cells, which are known as 'classical' antigen presenting cells), T-cells (T-lymphocytes) and B-cells (B-lymphocytes). B-cells have a capacity to present antigens to T-cells, in a manner which is in several respects analogous to presentation by conventional antigen presenting cells. It is during this B-cell T-cell interaction that B-cells acquire the 'help' needed to produce specific antibodies. Unlike classical antigen presenting cells however, B-cells are not good at acquiring particulate antigens. Some B-cells however (i.e., those which are specific for a given antigen) are particularly good at antigen presentation because they are able to acquire and concentrate small antigen particles (including antigen molecules) via their antigen-specific surface-immunoglobulin immunoglobulin receptors. Compared to non-antigen specific B-cells, antigen specific B-cells are at least 1000× more efficient at presentation of antigen to class-II restricted T-cells (Lanzavecchia, A., Antigen-specific interaction between T and B cells, *Nature* (1985) April 11-17:314(6011):537-539), Antigen specific B-cells may therefore be important targets for the compositions of the present invention, since they have the capacity to acquire particles of antigenic protein and its associated DNA.

T-cells and B-cells recognize antigens in different ways. These differing modes of recognition have implications for the differing modes of embodiment of the present invention. In order to understand the favourable embodiments of the invention it is first necessary to appreciate the features of these differing modes of recognition. T-cells recognize peptide fragments of proteins embedded in class-II or class-I MHC antigens at the surface of cells, whereas B-cells (which ultimately produce antibody) recognize surface features of the unfragmented antigen (which is usually protein in character), via antibody-like antigen receptors on their cell surfaces. The differing recognition requirements of T-cells and B-cells are reflected in the differing nature of their epitopes. Thus whereas B-cells must recognize surface features of an antigen or a pathogen (B-cell epitopes), T-cell epitopes (which comprise peptides of about 8-12 amino acids in length), are not obliged to be present on the surface of a antigen, and may be 'internal' as well as 'external' when viewed in the context of the three-dimensional structure of the antigen. According to the 'specific theory' of the present invention (as defined above), the most favored sitting of a B-cell epitope is 'surface' on the antigen or pathogen, which facilitates the uptake and stimulation of antigen-specific B-cells by appropriately formulated liposomal [nucleic-acid+protein]. However, according to the general theory of the invention (where liposomes are acquired in a non-antigen-specific manner by antigen presenting cells), an epitope (particularly a T-cell epitope) may be sited internally in the structure of the antigen, and is not required to be available or exposed on the surface of the antigen or agent.

In one favorable embodiment of the invention both antigenic protein and assistor protein are derived from a surface antigen of a viral protein. The proteins may have the same sequences as one another or may be mutated, may have portions deleted, or may be fused with other polypeptides, provided that they share at least one epitope (B-cell or T-cell) preferably several.

The portions of protein which the antigenic protein and the assistor protein have in common may be expressed in terms of their sequence homologies. It is believed that the proteins should be such that the assistor protein has at least one contiguous sequence of at least ten residues having at least 50%, preferably at least 75%, more preferably at least 90%, similarity with a contiguous sequence of the same length of the antigenic protein. Generally the respective contiguous sequences are at least fifty residues long, and have at least 90% sequence similarity, preferably at least 75% sequence similarity. More preferably the said contiguous sequences have at least 50%, preferably at least 75% more preferably at least 90% sequence identity.

Sequence similarity is only one index of structural similarity however, and in the case of the 'special theory' (defined above) it is necessary only that the assistor protein and the encoded and expressed protein share a single B-cell epitope (defined as recognized by a single antibody recognizing the agent) without any requirement for sequence homology.

The compositions of the invention are useful for generating an immune response, for instance which is sufficient to resist infection, by an infectious agent. The antigenic protein and assistor protein are thus preferably derived from a source which is an infectious agent, for instance a microorganism such as a bacterium, or a virus. Suitably the virus is a conventional virus, (as distinct from a protein-only infectious agent such as a prior), against which immune responses are known (or believed to be) capable of neutralising or eliminating the virus, for instance a hepatitis virus (such as hepatitis-B or C viruses) or an influenza virus (such as influenza-A or B viruses). Suitably the infectious agent may be a bacterium, such as a *streptococcus* (e.g., *Streptococcus pneumoniae*, or a member of the group-A or group-B streptococci) or an agent capable of causing meningitis such as the meningococci groups A, B & C or *Haemophilus influenza*, or organisms capable of causing ear infections in children such as *Moraxelia cattharadis*. Suitably the agent may be a *mycobacterium* such as *Mycobacterium tuberculosis*. Suitably the antigen may also be a host protein that is selectively expressed on or within cancerous cells or tissues, such as carcinoembryonic antigen, or CD55 (a complement control protein), or an integrin or other marker of the tumour vasculature. The target antigen of this novel vaccine composition may also be a host protein or peptide requiring neutralisation or elimination such as a harmful autoantibody, or a peptide such as the amyloid beta peptide of Alzheimer's disease in its various forms (A-beta 40 and A-beta 42).

The target antigen of the vaccine may also be a carbohydrate, such as a bacterial polysaccharide, wherein the expressed form of the protein and/or the assistor protein mimic(s) the antigenic structure of said carbohydrate antigen. Suitable peptide mimics of the group-B meningococcal polysaccharide (Laing, Granoff Granoff D M and Moe G R. Molecular mimetics of meningococcal B epitopes. U.S. Pat. No. 6,030,619) and of group-B streptococcal polysaccharide have been described. Such peptides may be expressed as concatenated forms where the different peptide sequence embodiments of the carbohydrate epitope are joined together at the DNA level to form a polypeptide or protein comprising repeating epitopes of different sequence.

According to the present invention, the target epitope(s) against which a beneficial immune response is desired should correspond to epitope(s) which are shared between the protein encoded by the DNA and the assistor protein. The location of the target epitope(s) in situ on the target antigen may be accessible to antibodies (such as neutralising epitopes of the influenza-A hemagglutinin), but alternatively may usefully also be internal in the agent (such as a heat shock protein of *Mycobacterium tuberculosis*).

The assistor protein, though usually being highly similar or identical to the nucleic-acid encoded protein in the composition, may be whole virus (virion) or a 'split' virus preparation (such as well known detergent-lysed influenza virus preparations) provided that it contains a protein which has at least one (and preferably several) shared epitopes with the nucleic-acid encoded protein. The assistor protein would generally not be comprised of a viable virus capable of replication in a host animal.

In the invention the nucleic acid may be RNA, but is preferably DNA. DNA operatively encoding an antigen should preferably comprise a promoter and, preferably, control sequences. Suitably the DNA is plasmid DNA, conveniently derived from *E. coli* C1 plasmid, but could be linear DNA.

It may be desirable in the invention to include a nucleic acid that encodes for more than one protein and/or to include one or more different assistor proteins. For this embodiment, it is preferable that a single vesicle should have associated with it nucleic acid encoding for an antigenic protein which shares epitopes as described above with the antigenic or assistor protein associated with the particle. For example the composition of the invention may comprise two or more different liposome types in admixture, for instance one of which comprises nucleic acid encoding a first antigenic protein with a first assistor protein, the antigenic protein and assistor protein being related as described above, and a second liposome type comprising nucleic acid encoding a second antigenic protein associated with a second assistor protein related to the second antigenic protein as described above. Alternatively, a single liposome may contain two or more different nucleic acids, one of which encodes a first antigenic protein and the other of which encode a second antigenic portion (etc.), and first and second (etc.) assistor protein, the first and second assistor proteins being related to respective first and second antigenic proteins as described above. The two or more antigenic proteins may be part of the same expressed protein molecule (i.e., a fusion protein), encoded by a single nucleic acid. Alternatively, two or more separate nucleic acid components, each encoding different parts of one antigenic protein, may be included (with the protein) in a single liposome. A favourable composition may also comprise severally co-formulated DNAs and their cognate proteins (assistor proteins), provided that each DNA is associated with its cognate or assistor protein in the same liposome.

The same arrangement of nucleic acid and protein may be achieved in vesicular compositions of the invention formed from non-phospholipid components.

Embodiments involving more than one antigenic protein, as described in the preceding paragraph, may be of particular value where the composition is to be used to generate an immune response, generally vaccinate a subject, against an infective agent which may exist in several infective strains. This embodiment of the invention is of particular value where the infectious agent is a virus, especially an influenza virus. Thus the nucleic acid encoded antigenic proteins and their corresponding assistor proteins may be derived from A and B strains of influenza virus. One preferred embodiment would comprise two currently circulating (or anticipated) strains of influenza A, plus one currently circulating strain (or anticipated strain) of influenza-B. The composition would favourably comprise all six molecular entities associated with a single vesicle (e.g., a liposomal particle) such that each particle is associated with all three nucleic acids and all three proteins. Another favorable embodiment incorporating influenza viruses would comprise three separately created vesicular formulations comprising {Ai protein+AiDNA}:{Aii protein+AiiDNA} and {B protein+B DNA} (where curly brackets denote the payload of an individual vesicle) mixed together in a single dose or administrated in three separate doses to a recipient human or animal.

In one useful embodiment of the invention, the nucleic acid is at least partially, and preferably substantially wholly, entrapped within the intravascular space of vesicles, usually liposomes. When it is entrapped in the intravascular space, the nucleic acid is optimally protected from its environment, but may nevertheless be delivered into the appropriate cells once administered to a subject. Alternatively, but less preferably, the nucleic acid may be complexed with the vesicles that is primarily be associated on the external surface of the vesicles. Such an arrangement provides a lower degree of protection during administration and delivery of the nucleic acid, but may also be effective.

In one embodiment of the present invention the assistor protein is, preferably, at least in part, accessible at the outer surface of the vesicle. This will allow acquisition of the vesicle by antigen specific B-cells, and, following production of antibodies in the early stages of the immune response to the vaccine composition, will facilitate the uptake of antibody-complexed vesicles by antigen presenting cells via high affinity Fe-gamma receptors that recognize surface bound antigen-specific IgG on the vesicle surface. Likewise, surface located antigen on a liposomal or other vesicle will allow complement fixation, resulting in the uptake of vesicles and their fragments by complement receptors on antigen-presenting cells and B-cells. In order to achieve these results, the protein may be merely complexed with the external surface of the vesicle (e.g., by electrostatic or hydrophobic interactions, in the manner of an extrinsic membrane protein) or, preferably, is embedded in the wall of the vesicle (e.g., via a trans-bilayer hydrophobic sequence of polypeptide chain) remaining partly exposed to the extravesicle environment. In either instance, according to this embodiment, the epitope of interest should be accessible from the outside of the vesicle. Such accessibility may be determined by carrying out binding experiments using antibodies against the respective epitope. Such binding data demonstrating surface exposure are described in the figures associated with the text for our work on co-formulation of DNA and protein for influenza-A virus.

Where the vesicle is liposomal, the liposome forming components used to form the liposomes may include neutral, zwitterionic, anionic and/or cationic lipid moieties. These may be used in relative amounts such as to confer an overall charge on the liposome or, less preferably, the liposomes may have no overall charge. It is found that using lipid components such that the liposome has an overall positive charge can provide good results (refer to the data section of the application). In addition to components which are properly termed lipids (including glycerides and cholesterol), the liposome forming components may include non-lipidic components (i.e., which are not naturally occurring lipids) such as non-ionic or cationic surface active agents.

According to a particularly preferred embodiments of the invention, the new composition comprises liposomes formed from liposome forming components including at least one cationically charged component in an amount such that the liposomes have an overall positive charge.

In this embodiment of the invention the cationic component incorporated into the liposome may be any of those which have been used in liposome preparation for improving transfection rate by complexation with polynucleotides. The component may be a lipidic or a non lipidic compound and may be synthetic or natural. Preferred cationic lipids are 1,2-bis(oleoyloxy)-3-(trimethylammonio)propane (DOTAP), 1,2-bis(hexadecyloxy)-3-trimethylaminopropane (BisHOP), N-[1-(2,3-dioleyloxy)propyl]-N,N,N-triethylammoniumchloride (DOTMA) and other lipids of structure I defined in U.S. Pat. No. 4,897,355, incorporated herein by reference or the ester analogues.

The structure is a follows:

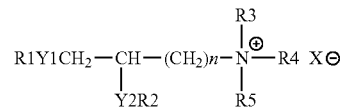

or an optical isomer thereof, wherein Y1 and Y2 are the same or different and are each —O— or O—C(O)— wherein the carbonyl carbon is joined to R1 and R2 as the case many be; R1 and R2 are independently an alkyl, alkenyl, or alkynyl group of 6 to 24 carbon atoms, R3, R4 and R5 are independently hydrogen, alkyl of 1 to 8 carbon atoms, aryl or aralkyl of 6 to 11 carbon atoms; alternatively two or three of R3, R4 and R5 are combined with the positively charged nitrogen atom to form a cyclic structure having from 5 to 8 atoms, where, in addition to the positively charged nitrogen atom, the atoms in the structure are carbon atoms and can include: one oxygen, nitrogen or sulfur atom; n is 1 to 8; and X is an an ion.

Preferred embodiments are compositions wherein R1 and R2 individually have from 0 to 6 sites of unsaturation, and have the structure

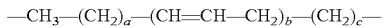

$$-CH_3-(CH_2)_a-(CH=CH-CH_2)_b-(CH_2)_c-$$

wherein the sum of a and c is from 1 to 23; and b is 0 to 6. Most preferably each of R1 and R2 is oleyl. Particularly preferred embodiments are compositions where the long chain alkyl groups are fatty acids, that is, wherein Y1 and Y2 are alike and are —O—C(O)—

Alternatively cationic lipids of the general structure I or the general structure II defined in U.S. Pat. No. 5,459,127, incorporated herein by reference may be used.

Other suitable cationic compounds are the non-lipid component stearylamine and 3β[N-N'N'-dimehtylamino ethane)-carbanyl] cholesterol (DC-Chol) (a lipidic component) or analogues thereof.

The liposomes, in addition to comprising cationic components, generally also comprise non-ionic and/or zwitterionic components which include lipids, which may be phospholipids or other lipids not including phosphoryl groups. Preferably the lipids include phospholipids, such as natural or synthetic phosphatidylcholines, phosphatidyl ethanolamines, phosphatidylserines in any of which the long chain alkyl groups (which may be joined through ester or ether linkages) may be saturated or unsaturated. Preferably the acyl group of glyceride lipids are unsaturated. The components may include non-lipidic components, for instance non-ionic surfactants such as sorbitan mono esters of fatty acids, and/or ethoxylated fatty acids or other analogues, such as ethoxylated lanolins.

Best results are achieved when the liposomes include fusogenic lipids, which are usually phosphatidyl ethanolamines in which the acyl groups are unsaturated. Cholesterol may be included although it may render the liposomes too stable for adequate delivery of polynucleotide into target cells.

The amount of cationic component is preferably in the range 5 to 50% of the total moles of liposome forming components, preferably in the range 10 to 25% mole.

A vesicle composition is generally in the form of an aqueous suspension for instance, in a physiological buffer. Alternatively it could be a dried composition for rehydration.

The composition is preferably a vaccine, for instance adapted for administration by subcutaneous, intravenous, intramuscular, intradermanl, nasal, oral, other mucosal or pulmonary routes.

The vesicles may be made by any of the generally used vesicle-forming techniques. The vesicles may be multilamellar or unilamellar vesicles and may be relatively large (vesicle diameters in the range 300 nm to 5000 nm; preferably less than 2000 nm, preferably with average diameters in the range 500-1000 mm), or small (vesicle diameters in the range 100 nm to 400 nm preferably with average diameters in the range 200 to 300 nm). Preferably the vesicles have a mean diameter not exceeding 500 nm, and preferably substantially all have diameters less than 2000 nm.

Although a liposomal composition of the invention may be formed by conventional liposome forming processes, such as by dispersing the liposome forming materials from a film into a suspending medium containing the nucleic acid and the protein, following by one or more size adjusting steps, or alternatively by co-dissolving liposome forming materials and nucleic acid and/or assistor protein in a common solvent followed by a liposome forming step involving addition of aqueous liquid, or by loading nucleic acid and/or assistor protein through the walls of performed liposomes using concentration gradient electroporation or electrophoretic techniques, a preferred method uses a dehydration-rehydration technique.

Several suitable methods of liposomal formulation are described in the book-chapter by Christopher J. Kirby and Gregory Gregoriadis: ISBN 0-471-14828-8 *Encyclopedia of Controlled Drug Delivery* Editor: Edith Mathiowitz, Published July 1999 by Wilsey Chapter 'L' for liposomes. These include (non-exhaustively) multi-lamellar liposomes prepared by the 'hand shaken' method; dehydration/rehydration vesicles (the method used in the present examples, which is highly efficient); and simple hydration of solvent-solubilized lipids. The simultaneous presence of DNA and protein in these procedures will result in various degrees of co-entrapment and other forms of association of both entities with the liposomes. Calcium phosphate may also be used to precipitate DNA and protein together resulting in a 'protein co-formulation with DNA' version of our invention described in WO-A-0141739.

Another favored method for the formation of associated DNA and its cognate protein is that published by Judith Senior and Gregory Gregoriadis (*Biochimica et Biophysica Acta* (1989) 1003:58-62). This is a variant of the dehydration-rehydration method wherein the 'assistor protein' component of the present invention may be incorporated by covalent conjugation onto the surface of small unilamellar vesicles (SUV). Such SUV are then lyophilised, and then re-hydrated according to Senior and Gregoriadis (above), in a solution of the antigen-encoding DNA. The resulting multi-lamellar vesicles have most of the protein payload on the surface of the liposomal particle, which is a favoured embodiment of the present invention.

A process according to the invention for forming a liposomal composition comprises the steps
 a) providing an aqueous suspension of small unilamellar vesicles (SUVs) formed of liposome forming materials;
 b) contacting the aqueous suspension of SUVs with nucleic acid with operatively encodes and antigenic protein to form an SUV-nucleic acid suspension;
 c) dehydrating the SUV-nucleic acid suspension to provide a dehydrated mixture; and
 d) rehydrating the dehydrated mixture in an aqueous resuspending medium to form a suspension of nucleic acid containing liposomes,
 including the step of introducing an assistor protein whereby the nucleic acid containing liposomes are associated with said assistor protein.

The dehydration-rehydration method results in nucleic acid being entrapped within the intravascular space of the produce liposomes. Additionally a small amount may be left on the outside of the liposomes. The assistor protein may be added at various different stages of the process. It may be contacted with the aqueous suspension of SUVs before, during or after step b and before step c. The assistor protein will become coentrapped within the intravascular space of the liposomes with nucleic acid.

In an alternative process, the assistor protein is present in the resuspending medium during the rehydration step. In this embodiment, at least a part of the protein is likely to be exposed on the external surface of the liposomes. In an alternative process, the protein may be contacted with the aqueous suspension of nucleic acid containing liposomes.

This embodiment will result in substantially all of the protein being associated with the external surface of the liposomes.

In order to increase the degree of incorporation of protein, whilst still allowing exposure of epitopes at the external liposome surface, it may be desirable in some embodiments to conjugate the assistor protein to a lipophilic moiety which is suitable for embedding within the wall of the liposome, such as a fatty acyl moiety. The conjugation may comprise a part of the preparation procedure for the assistor protein. Alternatively, the assistor protein may be chemically conjugated to a component of the liposome after step d.

Where the liposome forming materials include cationic moiety such that there is an overall cationic charge on the liposomes, there may be adequate electrostatic attraction between the positively charged liposomes and the assistor protein, where this has an overall negative charge under the ambient conditions such that hydrophobic protein is needed and complexation of the protein provides a strong enough association.

Preferably the liposome forming materials comprise at least 5% by mole cationic compound.

In the invention the weight ratio of nucleic acid to assistor protein is preferably in the range 1000:1 to 1:1 most preferably the ratio is in a range between ration 5:1 and 30:1.

The weight ratio of nucleic acid to liposome forming materials is preferably in the range of 1:100 to 1:1000, more preferably in a range of 1:100 to 1:300.

In the process of the invention, the liposomal particles used in step a) preferably have sizes in the range 30 nm to 5000 nm, most preferably substantially all of the liposomes having diameters less than 1000 nm. The process results in product liposomes having particle sizes in the range 200 nm to 5000 nm, preferably in the range 300 nm to 2000 nm. Where necessary, the process may involve a size-controlling feature. This may involve incorporation of components into the re-suspending medium which control the liposome size (such as sugars, as described in WO-A-0156548). Alternatively the size control may involve an additional step following step d, in which the suspension is subjected to microfluidisation, passage through filters or homogenisation. Sonication is a less preferred but viable option for this purpose but it results inevitably in some level of DNA fragmentation.

After the process, it is preferable for the product liposomes, comprising both nucleic acid and protein, to be subjected to a purification step, in which non-entrapped nucleic, or assistor protein, or other components, are removed from the product suspension. Such purification processes may involve centrifugations, filtration, passage through a porous membrane of defined pore size, gel-exclusion chromatography, such as size exclusion chromatography, where the vesicles appear in the void volume.

We have found that the present invention is highly effective for generating an immune response when administered to a subject, particularly an improved antibody response. We believe the improvement exhibited by the present invention to be due fundamentally to the co-targeting of nucleic acid and assistor protein to the same antigen presenting cells, (possibly including antigen specific B-cells), such that following encounter with a suitably formulated vesicle an individual antigen presenting cell takes up both the nucleic acid and its cognate protein. In the case of the influenza hemagglutinin, we observe that separate formulation of nucleic acid (DNA encoding hemagglutinin) and its cognate protein (hemagglutinin protein) in separate liposomal compartments or populations, followed by mixing and co-administration in vivo, does not achieve the synergistic effect of co-formulation of the DNA and its cognate protein in the same liposomal particles such that each liposome contains both DNA and its cognate protein. These data support our hypothesis that the surgery of DNA with its cognate protein in eliciting an immune response (in this case against the influenza hemaggutinin) requires the appropriate formulation to allow co-targeting of both DNA and its cognate protein to the same antigen presenting cell.

EXAMPLES

The present invention is illustrated in the accompanying examples:

Example 1

Haemagglutinin in Cationic Liposomes

Materials and Methods:
Lipids

Egg phosphatidylcholine (PC). Dioleoyl phosphatidylethanolamine (DOPE) and 1,2-dioleoyl-3-(trimethylammonium) propane (DOTAP) were purchased from Sigma Chemical Co., UK. All lipids were stored (−20° C.) dissolved in chloroform, purged with nitrogen.

DNA

Plasmid pCI-OVA (ref DNA OVA) (a kind gift of Dr. T. Nagata, Hamamatsu University School of Medicine, Japan) contains the chicken egg albumin protein (ovalbumin, OVA) (Yoshida A. Nagata T, Uchijima M. Higashi T, and Koide Y. "Advantage of gene gun-mediated over intramuscular inoculation of plasmid DNA vaccine in reproducible induction of specific immune response." *Vaccine* (2000) 18:1725-1729) cDNA cloned at the EcoRI site of the pCI plasmid (Promega, Madison, Wis.) downstream from the CMV enhancer/promoter region. Plasmid P1.17/SichHA (ref DNA HA) was provided by Dr. J. Robertson (NIBSC, UK) (Johnson, P., et al., *J. Gen. Virol.* (2000) 1737-1745) containing the full length HA from influenza A/Sichuan/2/87. Both plasmids for dosing were commercially produced by Aldevron (Fargo, USA) and contained <100 Endotoxin Unit (EU)/mg of DNA with no residual protein detectable.

Proteins

Influenza A/Sichuan/2/87 whole inactivated virus protein (sucrose gradient purified, major protein HA, ref antigen HA) was obtained from the NIBSC, UK. Ovalbumin (Grade VI, ref antigen OVA) were purchased from Sigma Chemical Co., UK.

Preparation of Liposome Compositions

Briefly, small unilamellar vesicles (SUV) were prepared from egg phosphatidylcholine (PC) and dioleoyl phosphatidylcholine (DOPE) and 1,2-dioleoyloxy-3-(trimethylammonium) propane (DOTAP) (4:2:1 molar ratio) by sonication were mixed with DNA or protein alone or DNA and protein together (Table 1). Formulations were prepared in triplicate, two vials for dosing (prime and boost) and one vial for % entrapment calculations based radio labeled tracer (HA and OVA, DNA and protein) added to materials for entrapment and freeze-dried overnight as described in Gregoriadis, G., Saffie, R. and Hart, S. L., "High yield incorporation of plasmid DNA within liposome; effect on DNA integrity and transfection efficiency,"*J Drug Targeting* (1996) 3:467-475 and in Kirby, C., Gregoriadis, G., "Dehydration-rehydration vesicles (DRV): A new method for high yield drug entrapment in liposomes", *Biotechnology* (1994) 2:979-984. Following rehydration under controlled conditions, the generated dehydrated-rehydrated vesicles (DRV liposomes) were washed by centrifugation to remove non-incorporated DNA. The washed pellets were resuspended in PBS to the required dose volume. DNA and/or protein incorporation into liposomes was estimated on the basis of $^{35}S$ (for DNA) and $^{125}I$ (for protein) radioactivity recovered in the suspended pellets. Liposomes were subjected to microelectrophoresis and photon correlation spectroscopy (PCS) at 25° C. in a Malvern Zetasizer 3000 to determine their zeta potential (ZP) and z-average diameter respectively.

TABLE 1

Formulation

| Group | DNA μg | Antigen μg | Liposome (PC:PE:DOTAP μmole) | % Entrapment DNA | % Entrapment Protein |
|---|---|---|---|---|---|
| 1.1 | 70(HA) | 4.2(HA) | 11.2:5.6:2.8 | 100 | 99.5 |
| 1.2 | 70(OVA) | 4.2(HA) | 11.2:5.6:2.8 | 91.3 | 84.1 |
| 1.3 | 70(HA) | 5.25(OVA) | 11.2:5.6:2.8 | 97.5 | 99.0 |
| 1.4 | 70(HA) | | 11.2:5.6:2.8 | 100 | — |
| 1.5 | | 4.2(HA) | 11.2:5.6:2.8 | — | 89.8 |

Animal Procedures

Female Balb/c mice 6-12 weeks old (Harlan, UK) were immunised by subcutaneous injection administered in 0.2 ml dose volume (table 2). Final dose quantities were calculated based on % material (DNA, Protein or both) entrapped (from radioactivity count vials). Negative control mice received doses of PBS respectively. Mice received two doses of antigen at days 0 and 28, with sample bleeds collected from the tail vein at day 16, 28 and 42 with respect to the first injection.

Formulation Capture ELISA

Formulations for immunisation (Table 2) were assayed by capture enzyme-linked immunoadsorbent assay (ELISA) for HA (A/Sichuan) antigenicity. Certified binding chemistry 96 well plates were coated overnight at 4° C. with 50 μl/well of 1:2000 dilution of sheep anti A/Siebuan HA reference sera (NIBSC) in carbonate buffer (pH 9.6). After removing the sheep antibody solution, wells were coated with 200 ul of 10% (w/v) FCS (Fetal Calf Sera) in PBS. After 2 h at 37° C., the blocking solution was removed and serially diluted (x2 series) formulations (ref Table 2) were added to the wells (50 μl sample/well). Formulations were diluted in PBS and Triton X100 (Tx-100) which is capable by lysing liposomal formulations to reveal entrapped materials (5) Gregoriadis, G. Brenda McCormack, Mia Obrenovic, Roghieh Saffie, Brahim Zadi, and Yvonne Perrie, "Vaccine entrapment in liposomes", *Methods* (1999) 19:156-162). Following 1 h incubation at 37° C., plates were washed four times with PBS/Tween 20 and overlaid with dilutions of a murine specific (influenza A/Sichuan) antisera at a dilution 1/5000 (50 μl sample/well). Following 1 h incubation at 37° C., plates were washed four times with PBS/Tween 20 and overlaid 50 μl/well of rabbit anti-mouse Ig-HRP conjugated sera (Dako). After 1 h at 37° C., plates were washed four times with PBS/Tween 20 and overlaid with 50 μl/well of substrate solution o-phenylenediamine (Sigma, Fast OPD).

The reaction was stopped by adding 50 μl/well of stopping solution (3M Sulphric Acid) and the absorbance of each well at 490 nm was determined.

Sera ELISA

Sera obtained form sample bleeds were diluted 20-fold in PBS and kept at −20 EC until assayed by the enzyme-linked immunoadsorbent assay (ELISA). Certified binding chemistry 96-well plates were coated overnight at 40° C. with 50 μl/well of 1:1000 dilution of sheep anti A/Sichuan HA reference sera (NIBSC, UK) in carbonate buffer (pH 9.6). After removing the sheep antibody solution, wells were coated with 200 μl of 2% (W/V) BSA in PBS. After 2 h at 37° C., the blocking solution was removed and Influenza A/Sichuan/2/87 whole inactivated virus protein (sucrose gradient purified, major protein HA) 2.5 μg/ml (in PBS) were added to the wells (50 μl sample/well). Following 1 h incubation at 37° C. plates were washed four times with PBS/Tween 20 (trade mark) and overlaid with dilutions of the different experimental serum (individual animal sample bleeds or group sera pools) starting at dilution 1/100 (50 μl sample/well). Following 1 h incubation at 37° C., plates were washed four times with PBS/Tween 20 and overlaid 50 μl/well of rabbit anti-mouse Ig-HRP conjugation sera (Dako). After 1 h at 37° C., plates were washed four times with PBS/Tween 20 and overlaid with 50 μl/well of substrate solution o-phenylenediamine (Sigma, Fast OPD). The reaction was stopped by adding 50 μl/well of stopping solution (3M sulphuric acid) and the absorbance of each well at 490 nm was determined. The antibody response was expressed as the reciprocal serum dilution required for OD to reach a reading of 0.200 (end point dilution). Sera conversion criteria were established from negative control animals (see Table 3, group 12 response), x2 negative control (OD approximately 0.2 units).

TABLE 2

Dose Formulations

Dose/animal (0.2 ml subcutaneous)

| Group | Liposome | DNA (ug) | Antigen (ug) |
|---|---|---|---|
| 1.1 | Yes (co formulated) | HA (10) | HA (0.6) |
| 1.2 | Yes (co formulated) | OVA (11) | HA (0.6) |
| 1.3 | Yes (co formulated) | HA (10) | OVA (0.76) |
| 1.4 | Yes | HA (10) | Nil |
| 1.5 | Yes | Nil | HA (0.6) |
| 1.6 | Yes (admix 1.4 and 1.5) | HA (10) | HA (0.6) |
| 1.7 | Nil | HA (10) | OVA (0.76) |
| 1.8 | Nil | OVA (11) | HA (0.6) |
| 1.9 | Nil | HA (10) | HA (0.6) |
| 1.10 | Nil | HA (10) | Nil |
| 1.11 | Nil | Nil | HA (0.6) |
| 1.12 | Nil | Nil | Nil |

Results

These data show that the compositions give rise to highly efficient co-entrapment of DNA and protein, the presence of protein having only a minor negative effect on the efficiency of entrapment of DNA and vice versa.

Figure 2:
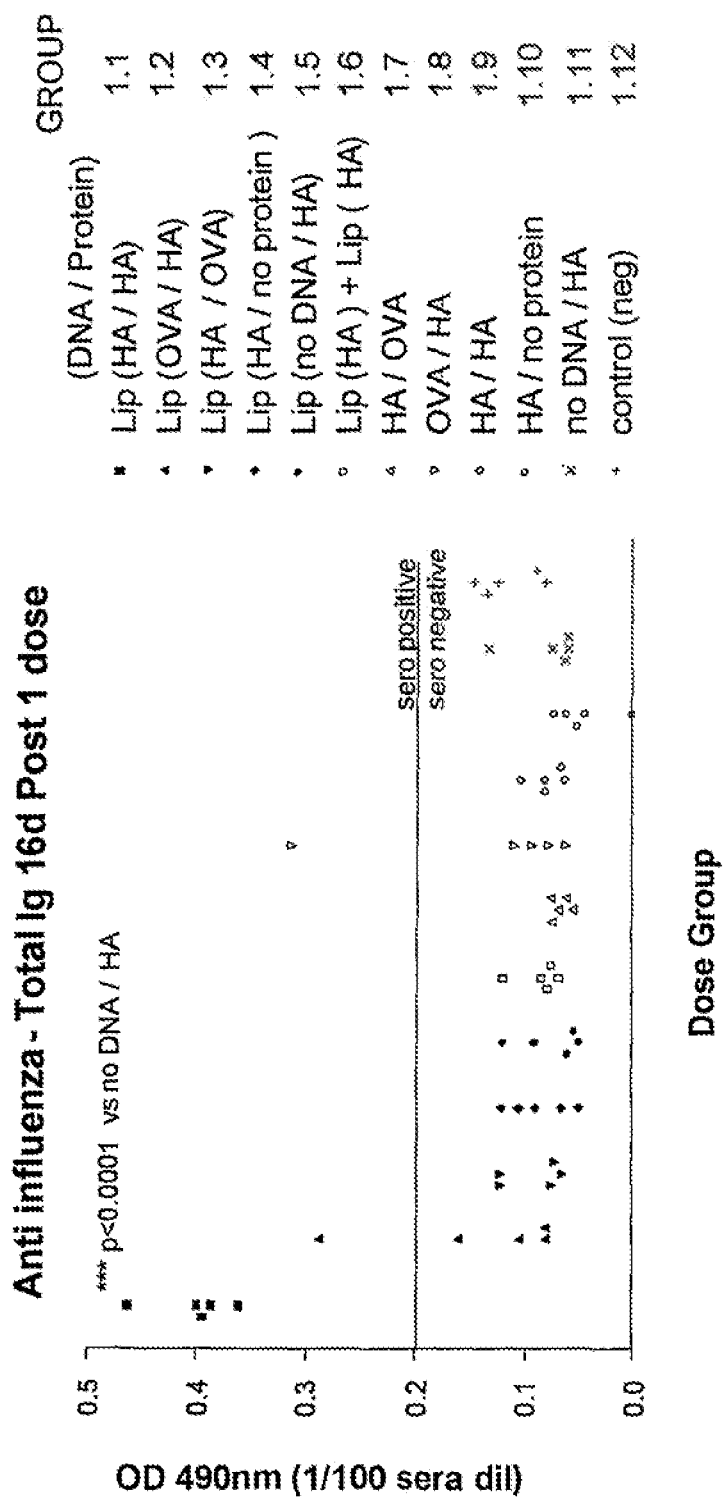
FIG. 2 shows measurement of and influenza (major protein HA) antibody response 16 days post one dose.
Figure 3:
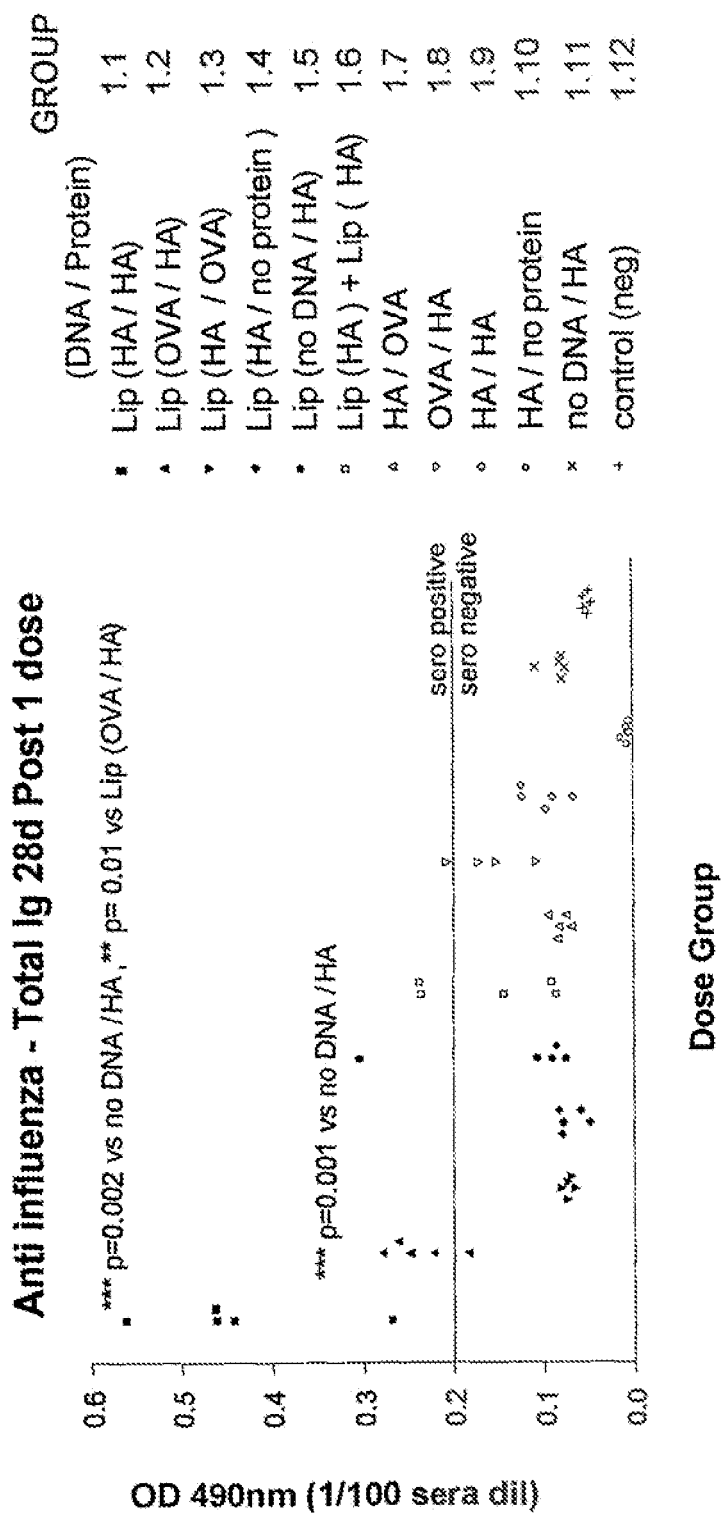
FIG. 3 shows measurement of anti influenza (major protein HA) antibody response 28 days post one dose.
Figure 4:
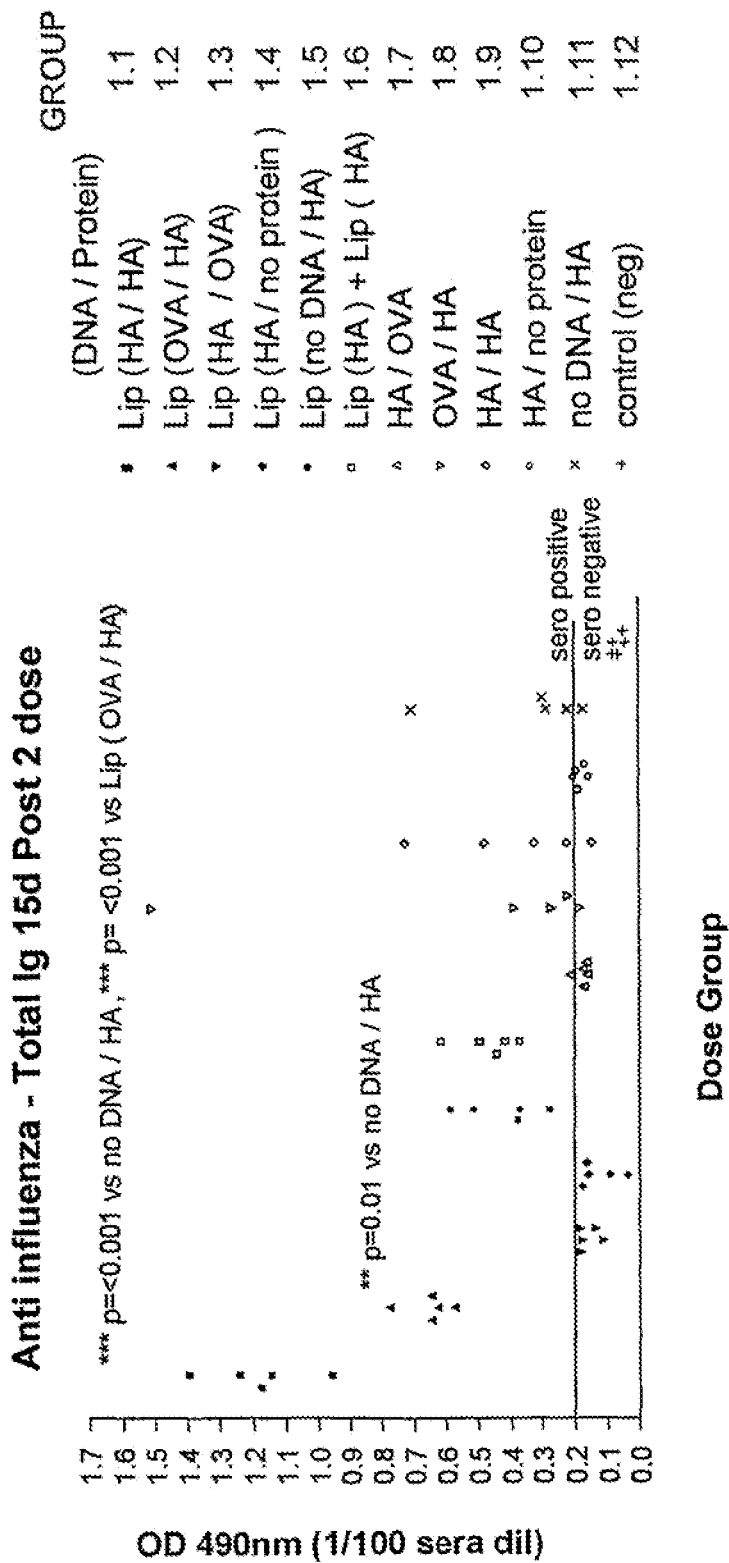
FIG. 4 shows measurement of anti influenza (major protein HA) antibody response 15 days post second dose.

Assessment of formulations for HA (Influenza A/Sichuan strain) antigenicity are shown in FIG. 1, OD490 nm signal is proportional to HA antigen. The sera antibody results for the twelve groups (Table 2) are shown in Table 3. The results are also illustrated in FIG. 2 (day 16), FIG. 3 (day 28) and FIG. 4 (day 42), day 15 following the second dose).

TABLE 3

| Group | | Formulation | | Total Ig anti A/Sichuan influenza antigen | | | | | | | | | | |
|---|---|---|---|---|---|---|---|---|---|---|---|---|---|---|
| 5 | | DNA | Antigen | 16 d post 1 dose | | | | 28 d post 1 dose | | | | 15 d post 2 doses | | |
| mice/grp | | 10 ug/dose | 0.6 ug/dose | OD | (+/−sem) | sero/5 | Titre | OD | (+/−sem) | sero/5 | Titre | OD | (+/−sem) | sero/5 | Titre |
| 1.1.1 | Lip( | HA | HA) | 0.400 | (0.017) | 5 | 675 | 0.457 | (0.053) | 5 | 1298 | 1.181 | (0.071) | 5 | 6015 |
| 1.2.1 | Lip( | OVA* | HA) | 0.142 | (0.039) | 1 | <100 | 0.240 | (0.017) | 4 | 150 | 0.656 | (0.034) | 5 | 1847 |
| 1.3.1 | Lip( | HA | OVA)** | 0.090 | (0.012) | 0 | <100 | 0.073 | (0.003) | 0 | <100 | 0.158 | (0.014) | 0 | <100 |
| 1.4.1 | Lip( | HA | nil) | 0.086 | (0.013) | 0 | <100 | 0.070 | (0.007) | 0 | <100 | 0.126 | (0.026) | 0 | <100 |
| 1.5.1 | Lip( | nil | HA) | 0.075 | (0.013) | 0 | <100 | 0.132 | (0.043) | 1 | <100 | 0.425 | (0.055) | 5 | 974 |
| 1.6.1 | | Lip(HA) | +Lip(HA) | 0.085 | (0.009) | 0 | <100 | 0.158 | (0.034) | 2 | <100 | 0.468 | (0.042) | 5 | 477 |
| 1.7 | nil | HA | +OVA | 0.067 | (0.004) | 0 | <100 | 0.080 | (0.004) | 0 | <100 | 0.176 | (0.009) | 1 | <100 |
| 1.8 | nil | OVA | +HA | 0.130 | (0.046) | 1 | <100 | 0.279 | (0.122) | 2 | 191 | 0.517 | (0.253) | 4 | 423 |
| 1.9 | nil | HA | +HA | 0.079 | (0.007) | 0 | <100 | 0.099 | (0.011) | 0 | <100 | 0.381 | (0.104) | 4 | 334 |
| 1.10 | nil | HA | nil | 0.046 | (0.012) | 0 | <100 | 0.007 | (0.002) | 0 | <100 | 0.180 | (0.009) | 1 | <100 |
| 1.11 | nil | nil | +HA | 0.078 | (0.014) | 0 | <100 | 0.083 | (0.006) | 0 | <100 | 0.336 | (0.096) | 4 | 298 |
| 1.12 | nil | nil | nil | 0.115 | (0.013) | 0 | <100 | 0.050 | (0.002) | 0 | <100 | 0.063 | (0.008) | 0 | <100 |

OD determined at $1/100$ sera dilution, sero (=sero conversion) >0.2 OD units at $1/100$ sera dilution, Titre = dilution sera yielding OD Value 0.2
OD units (measured on pool of individual sera/group)
*dose 11 μg
*dose 0.76 μg Discussion Assessment of the formulations (Table 2) for HA antigenicity by capture ELISA (FIG. 1) was preformed on formulations in the absence and presence of Triton X100 a liposome disrupting agent (note:—groups 1.3, 1.4, 1.7, 1.10 and 1.12 serve as negative controls for the assay as these formulations do not contain HA protein). Formulations tested in the absence of TX100 indicate HA antigen readily detectable in formulations containing HA in which the protein is not formulated with Liposomes (Groups 1.8, 1.9, 1.10), with a small HA antigen positive signal detectable for formulations 1.1 and 1.2, presumably generated by surface exposure of HA antigen capable of being bound by antibodies employed in this assay. In the presence of TX100 a substantially greater positive signal is obtained for Liposomal groups 1.1 and 1.2, indicating detection of antigen previously (cf without TX100) contained within the Liposomal formulation. Whilst formulation 1.5 and 1.6 both contain HA antigen entrapped by Liposomes in the absence of DNA in the formulation (cf 1.1 and 1.2) little HA antigenicity can be resolved.

The immune response generated following immunization with formulations (Table 2) was assesses by measurement of anti influenza (major protein HA) antibody response. Results are summarized in Table 3 and also illustrated in FIGS. 2, 3 and 4. Formulation 1.1 which consisted of both HA DNA and protein co-delivered in the same liposomal formulation produces a greater response than all the other formulations at each sera sample bleed tested (day 16, day 28 and day 42 (day 15 following the second dose)). The response for this co-delivered formulation is greater in terms of magnitude. (OD490 nm $1/100$ dilution sera and Titre) and number of animals deemed sera positive at each bleed point.

Formulations 1.2 and 1.3 which also consist of co-delivered protein and DNA in the same liposomal formulation fail to generate as substantial response as formulation 1.1. Formulations 1.2 and 1.3 consist of protein and DNA non cognate to each other.

Formulation 1.6 provides further indication of this invention, in that in terms of protein and DNA product administered to the animal formulation 1.1 is equivalent to 1.6. However in formulation 1.1 the products are co-delivered in the same liposomal vehicle whilst in formulation 1.6 the DNA and protein are delivered in separate liposomal vehicles. Again as stated previously the immune response to formulation 1.1 is substantially greater than 1.6.

The response to HA DNA containing formulations, excluding 1.1, (Formulations 1.3, 1.4, 1.7 and 1.10) essentially fail to generate an immune response, however this response may be dose related as Johnson, P., et al., J. Gen. Virol. (2000) 1737-1745 have reported positive response to this plasmid following immunisation (non-entrapped).

The adjuvant effect of liposomes for protein delivered in liposomal formulations (Formulation 1.5, versus Formulation 1.11) previously reported (Gregoriadis G. Tan L, Ben-Ahmeida E T, Jennings R., Vaccine (1992) 10(11):747-753) is weekly visible in the 15d post 2 dose sample bleed and again dose and immunisation schedule differences may account for different experimental results. The immunoadjuvant action of plasmid DNA in liposomes previously reported (Gursel M, et al., Vaccine (1999) 17:1376-1383) is also demonstrated in the difference in responses to formulation 1.2 and 1.5. However, the synergistic effect of co-formulation of hemagglutinin protein with its appropriate (cognate) plasmid far exceed any effect attributable to the well-known immunoadjuvant effects of DNA such as those observed by Klinman (Klinman D., et al., Vaccine (1999) 19:25 19-26) for CpG motifs.

Whilst the results presented are obtained following sub-cutaneous administration of the liposomal formulation, the proposed mechanisms of action, general and specific (plus antigen kinetics properties), should be effective by alternative routes of administration; intravenous, intra-muscular, intradermal, via nasal/pulmonary and oral routes, etc. Indeed liposomes have been successfully used by these routes to deliver both proteins and DNA, and generate immune response.

In summary we have found that the present invention is highly effective for generating an immune response when administered to a subject. The response involves an antibody response. The improvement exhibited by the present invention involved compositions of liposome forming materials and, associated with the liposomes, nucleic acid operatively encoding an antigenic protein and co-delivered protein, wherein the co-delivered protein shares epitopes with the antigenic protein.

Example 2

Mannose Targeted Hepatitis B Vaccine

Materials and Methods
Lipids

Egg phosphatidylcholine (PC), Dioleoyl phosphatidyl-ethanolamine (DOPE) and 1,2-dioleoyl-3-(trimethylammonium) propane (DOTAP) were purchased from Sigma Chemical Co., UK. N-[2-(2-[2-[2-(2,3-Bis-octadec-9-enyloxy-propoxy)-ethoxy]-ethoxy]-ethoxy)-ethyl]-3-(3,4,5-trihydroxy-6-hydroxymethly-tetrahydro-pyran-2-ylsulfanyl)-propionamide (formula given below (DOGP4αMan, a kind gift from Dr. Francis Schuber (Université Louis Pasteur Strasbourg I. Faculteé de Pharmacie 74, route du Rhin, BP 24 67401 Illkirch Graffenstaden)). All lipids were stored (−20 C.) dissolved in chloroform, purged with nitrogen.

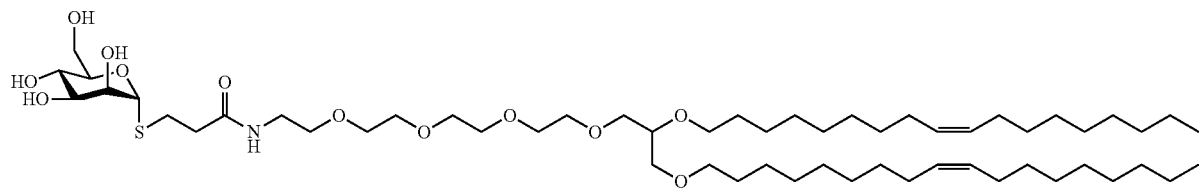

$C_{56}H_{107}NO_{12}S$
Exact Mass: 1017.75
Mol. Wt.: 1018.51
C, 66.04: H, 10.59; N, 1.38; O, 18.85; S. 3.15

DNA

Plasmid pRc/CMV-HBs(S) (or simply pCMV-S) expresses the hepatitis B surface antigen (small, or S, protein) under the control of the CMV immediate-early promoter (Davis, H. L., Michel, M. L., Whalen, R. G., "DNA-based immunization for Hepatitis B induces continuous secretion of antigen and high levels of circulating antibody," *Human Molecular Genetics* (1993) 2:1847-1851). Plasmid for dosing was commercially produced by Aldevron (Fargo, USA) and contained <100 Endotoxin Unit (EU)/mg of DNA with no residual protein detectable.

Proteins

Hepatitis B Surface Antigen (HBsAG) Recombinant protein, Purity: >95% by SDS-PAGE, purified from yeast Hansenula polymorpha (purchased from Aldevron, Fargo, USA. Lot 05/00 HBsAg).

Preparation of Liposome Composition

Briefly, small unilamellar vesicles (SUV) were prepared from egg phosphatidylcholine (PC) and dioleoyl phosphatidylcholine (DOPE), 1,2-dioleoyloxy-3-trimethyl-ammonium) propane (DOTAP) and N-[2-(2-{2-[2-(2,3-Bis-octadec-9-enyloxy-propoxy)-ethoxy]-ethoxy}-ethoxy)ethyl]-3-(3,4,5-trihydroxy-6-hydroxymethyl-tetrahydro-pyran-2-ylsulfanyl)-propionamide) (DOGP4αMan) (4:2:1:1 molar ratio) by sonication were mixed with DNA and protein alone or DNA and protein together (Table 4). Formulations were prepared in two vials for dosing (prime and boost) each vial contained radio labeled tracer (DNA and protein materials) added to materials to be entrapped (for % entrapment calculations) and freeze-dried overnight as described in Gregoriadis, G., Saffie, R. and Hart, S. L. High yield incorporation of plasmid DNA within liposome: effect on DNA integrity and transfection efficiency, J Drug Targeting, 1996, 5(6), 467-475 and in Kirby, C., Gregoriadis, G. Dehydration-rehydration vesicles (DRV): A new method for high yield drug entrapment in liposomes. Biotechnology. 1994, 2,979-984. Prior to freezing (pre freeze dry process) sucrose was added to each vial at an lipid to sucrose ratio (w/w) of 1:3 and allow to dissolve at RT (Brahim, Z. and Gregoriadis, G. A novel method for high-yield entrapment of solutes into small liposomes, J Liposome Research. 2000, 100(1), 73-80). Following rehydration under controlled conditions, the generated dehydrated-rehydrated vesicles (DRV liposomes) were diluted in PBS to the required dose volume. A volume (~25%) of each vial following rehydration was washed by centrifugation to remove non-incorporated materials. The percentage incorporation of DNA and/or protein into the liposomal formulation was estimated on the basis of $^{35}S$ (for DNA) and $^{125}I$ (for protein) radioactivity recovered in the suspended pellets. Liposomes were subjected to microelectrophoresis and photon correlation spectroscopy (PCS) at 25° C. in a Malvern Zetasizer 3000 to determined their zeta potential (ZP) and z-average diameter respectively.

TABLE 4

| | Formulation | | |
|---|---|---|---|
| Group | DNA µg | Protein (HbsAg) µg | Liposome PC:DOPE:DOTAP:DOGP4αMan µM |
| 2.1 | 464 | 13.28 | 42.6:21.3:5.3:5.3 |
| 2.2 | nil | 13.28 | 42.6:21.3:5.3:5.3 |
| 2.3 | 464 | Nil | 42.6:21.3:5.3:5.3 |

Animal Procedures

Female Balb/c mice 6-12 weeks old (Harlan, UK) were immunised by subcutaneous injection administered in 0.2 ml dose volume. Final dose quantities are summarised in Table 5. Mice received two doses of antigen at days 0 and 28, with sample bleeds collected from the tail vein at day (post 1 dose) and (post 2 doses) with respect to the first injection.

TABLE 5

| | Dose Quantity Total/animal | | |
|---|---|---|---|
| Group | DNA µg | Protein (HbsAg) µg | Lipid mg |
| 2.1 | 35 | 1 | 4.35 |
| 2.2 | nil | 1 | 4.35 |
| 2.3 | 35 | nil | 4.35 |

Sera ELISA

Sera obtained form sample bleeds were diluted in PBS and kept as −20° C. until assayed by the enzyme-linked immunoadsorbent assay (ELISA). Certified binding chemistry 96-well plates were coated overnight at 4° C. with 50 μl/well of Hepatitis B Surface Antigen (HBsAG) Recombinant protein at 2.5 μg/ml (Aldevron, Fargo, USA, Lot 05/00 HBsAg) in 0.1 M carbonate buffer (pH 9.6). After overnight incubation wells were washed four times with PBS/Tween 20™ (PBST) then wells were coated with 200 μl of 2% (w/v) BSA in PBS. After 2 h at 37° C., the blocking solution was removed and wells were washed four times with PBST and overlaid with dilutions of the different experimental serum (individual animal sample bleeds) starting at dilution 1/100 (50 μl sample/well). Following 1 h incubation at 37° C., plates were washed four times with PBST and overlaid 50 μl/well of rabbit anti-mouse Ig-HRP conjugated sera (Dako). After 1 h at 37° C., plates were washed four times with PBST and overlaid with 50 μl/well of substrate solution 3.3, 5.5 tetramethyl-benizdine (TMB, Pierce). The reaction was stopped by adding 50 μl/well of stopping solution (2M sulphuric acid) and the absorbance of each well at 450 nm was determined.

Results

The physical characteristics (% product (DNA and/or protein) entrapment, particle size and surface potential (Zeta)) are summarized in Table 6.

TABLE 6

| Group | Dose 1 % entrapment DNA | Dose 1 % entrapment Protein | Dose 2 % entrapment DNA | Dose 2 % entrapment Protein | Dose 1 Size nm | Dose 1 Zeta mV | Dose 2 Size nm | Dose 2 Zeta mV |
|---|---|---|---|---|---|---|---|---|
| 2.1 | 79.8 | 71.3 | 90.5 | 88.9 | 379 | 18.1 | 448 | ND |
| 2.2 | nil | 30.3 | nil | 58.3 | 166 | 18.5 | 134 | ND |
| 2.3 | 85.6 | nil | 94.5 | nil | 367 | 19.1 | 355 | ND |

ND = not determined.

The antibody responses (Sera ELISA) are expressed as the mean (n=5 animals/group) OD signal±SEM as the $Log_{10}$ serum dilution assayed. Results are expressed in FIG. 5, which shows the total 1 g results 28 days post one dose HbsAG, and FIG. 6, which shows the total 1 g results 28 days second dose.

Discussion

The use of mannose ligand targeted liposomes as delivery vehicles for DNA and protein for induction of an immune response has been described previously described (Kawakami S, Sato A, Nishikawa M, Yamashita F, Hashida m, *Gene Ther*. (2000) 7(4):292-299, and Latif N, Bachhawatt B K, *Immunol Lett* (1984) 8(2):75-78). Moreover the general utility of mannose receptor mediated uptake of antigen(s) (proteins) by antigen presenting cells is recognised as a powerful component in the induction of an immune response (Lanzavecchia, A., *Curr Opin Immunol* (1996) 8:348-354). The use of mannose ligand targeted liposomes to co-deliver both DNA and protein, within the same delivery vehicle (and likely to the same target cell) has not been reported.

Figure 5:
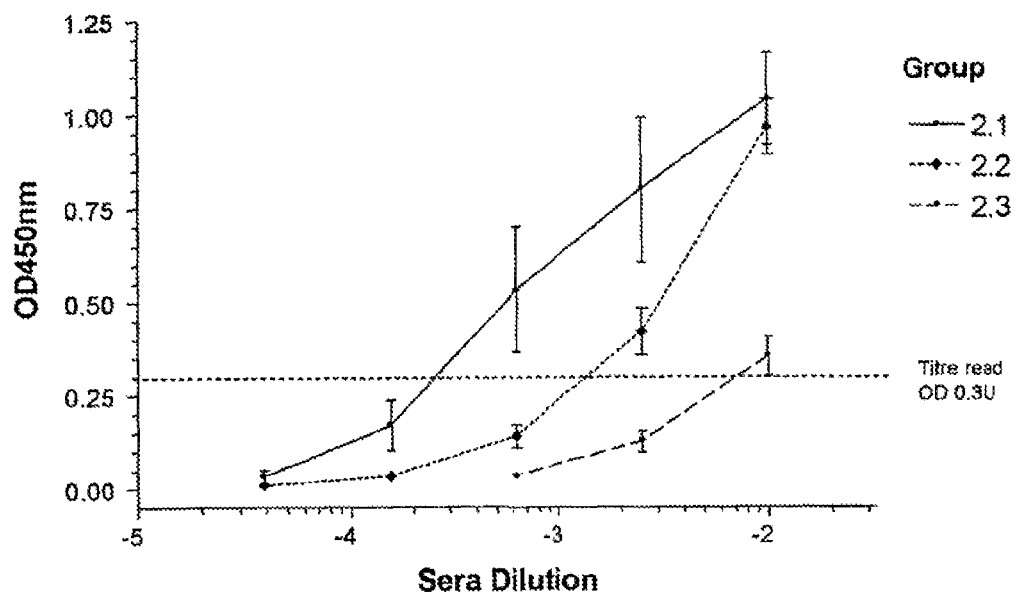
FIG. 5 shows the total 1 g results 28 days post one dose HbsAG.
Figure 6:
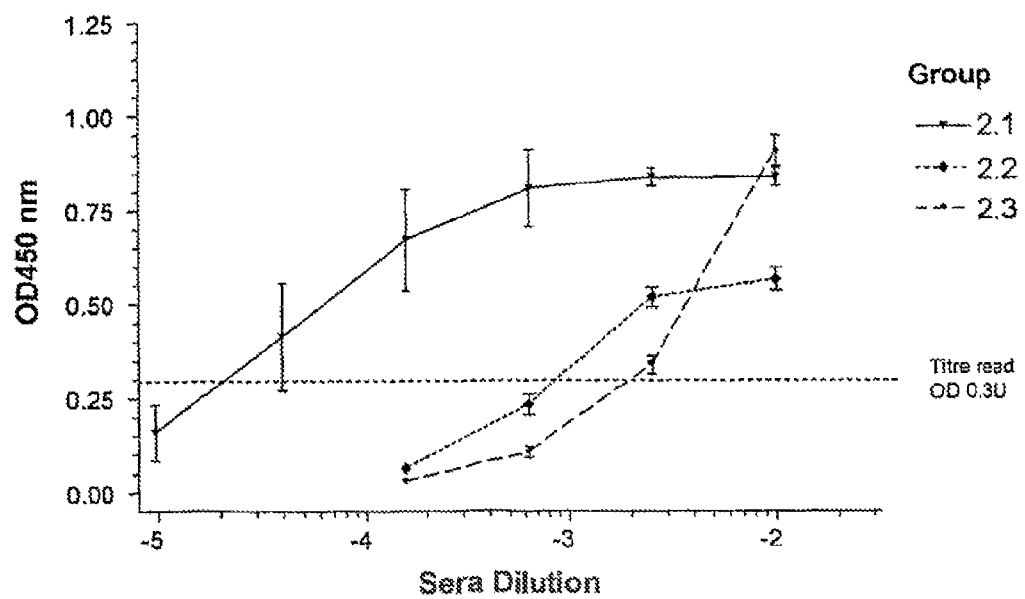
FIG. 6 shows the total 1 g results 28 days post second dose HbsAG.

The immune response generated following immunization with formulations (Tables 4 and 5) was assessed by measurement of anti Hepatitis B Surface Antigen (HBsAg) antibody response. Results are illustrated in FIGS. 5 and 6). Formulation 2.1 which consisted of both HA DNA and protein co-delivered in the same liposomal formulation produces a greater response than all the other formulations at each sera sample bleed tested (day 28 and day 56 (day 28 following the second dose)). The response for this co-delivered formulation is greater in terms of magnitude of both OD450 nm sera dilution and titre (endpoint read OD 0.3 units).

The response of the DNA containing formulations, excluding 2.1, Formulation 2.3, generate an immune response consistent with published results (Gregoriadis G. *Pharm Res*. (1998) 15(5):661-670) using the same DNA produce (at 10 μg DNA dose) in the same liposomal vehicle (PC:DOPE:DOTAP), without the mannose lipid (DOGP4αMan) component. The immunoadjuvant action of plasmid DNA in liposomes has been previously reported (Gursel, M., et al., *Vaccine* (1999) 17:1376-1383) using the same DNA (non encoding, ISS capacity control) and protein products as described herein. The reported adjuvant action of the DNA component for antigen-pDNA co-entrapped formulation in this paper is described as modest, at approximately 3 fold (Titre, post 2 doses results). The similar result exemplified (in FIG. 6), when a encoding (HBsAg) DNA component is used (Formulation 2.1) shows a 30 fold increase in response (cf formulation 2.2). Thus the synergistic effect of co-formulation of HBsAg protein with its appropriate (cognate) plasmid exceeds any effect attributable to the immunoadjuvant effects of DNA, approximately only 3 fold, such as those observed by Gursel or Klinman (Klinman, D, et al., *Vaccine* (1999) 19:25 1926) for CpG motifs alone.

In summary we have found that the present invention is highly effective for generating an immune response when administered to a subject. The response involves an antibody response. The improvement exhibited by the present invention involves composition of liposome forming materials including a mannosylated lipid component and, associated with the liposomes, nucleic acid operatively encoding an antigenic protein and a co-delivered protein, wherein the co-delivered protein shares epitopes with the antigenic protein.

Example 3

Protection from Influenza Virus Challenge

Material and Methods

Lipids

Egg phosphatidylcholine (PC), Dioleoyl phosphatidylethanolamine (DOPE) and 1,2-dioleoyl-3-trimethylammonium) propane (DOTAP) were purchased from Sigma Chemical Co., UK. All lipids were stored (−20° C.) dissolved in chloroform, purged with nitrogen.

DNA p1.18/PR8-HA (ref DNA HA) was provided by Dr. J. Robertson (NIBSC, UK) containing the full length HA from influenza A/Puerto Rico/8/34. Plasmid for dosing was commercially produced by Aldevron (Fargo, USA) and contained <100 Endotoxin Unit (EU)/mg of DNA with no residual protein detectable.

Proteins

Influenza A/Puerto Rico/8/34 whole inactivated virus protein (sucrose gradient purified, major protein HA, ref antigen HA) was obtained from the NIBSC, UK.

Preparation of Liposome Composition

Briefly, small unilamellar vesicles (SUV) were prepared from egg phosphatidylcholine (PC) and dioleoyl phosphatidyl-choline (DOPE) and 1,2-dioleoyloxy-3-(trimethylammonium) propane (DOTAP) (4:2:1 molar ratio) by sonication were mixed with DNA (ref DNA HA) and protein (ref antigen HA) see Table 7. Formulations were prepared in quadruplicate, two vials for dosing (prime and boost) and two vial for % entrapment calculations based radio labeled tracer (HA: DNA and protein) added to entrapped materials and freeze-dried overnight as described in Gregoriadis, G., Saffie, R. and Hart, S. L., "High yield incorporation of plasmid DNA within liposome: effect on DNA integrity and transfection efficiency," *J Drug Targeting* (1996) 3(6):467-475 and in Kirby, C., Gregoriadis, G., "Dehydration-rehydration vesicles (DRV): A new method for high yield drug entrapment in liposomes," *Biotechnology* (1994) 2:979-984. Following rehydration under controlled conditions, the generated dehydrated-rehydrated vesicles (DRV liposomes) were washed by centrifugation to remove non-incorporated DNA. The washed pellets were resuspended in PBS to the required dose volume. DNA and/or protein incorporation into was estimated on the basis of $^{35}S$ (for DNA) and $^{125}I$ (for protein) radioactivity recovered in the suspended pellets. Liposomes were subjected to microelectrophoresis and photon correlation spectroscopy (PCS) at 25° C. in a Malvern Zetasizer 3000 to determine their zeta potential (ZP) and z-average diameter respectively.

Animal Procedures

Female Balb/c mice 6-12 weeks old (Harlan, UK) were immunised by subcutaneous injection administered in 0.2 ml dose volume. Final dose quantities are summarised in Table 7. Mice received two doses on days 0 and 28, with sample bleeds collected from the tail vein at day 21 (post 1 dose) and 42 (post 2 doses) with respect to the first injection.

TABLE 7

| Group (formulation) | Dose Quantity Total/animal | | |
|---|---|---|---|
| | DNA µg | Protein (HA) (µg) | Lipid mg |
| 3.1 | 10 | 1.5 | 2.1 |
| 3.2 | 10 | 0.5 | 2.1 |
| 3.3 | 10 | 1.5 | Non-liposomally delivered, admixed (DNA + Protein) |
| 3.4 | nil | nil | nil (PBS) |

Live Influenza Virus Challenge

Mice were challenged at day 57, with respect to the first immunization, with approximately 10 $MID_{50}$ (50% mouse infective doses) in PBS with 2% (w/v) BSA of an mouse adapted live influenza virus (A/Puerto Rico/8/34) at the National Institute of Biological Standards and Controls. UK (NIBSC). The virus was administered to non-anaesthetized mice in 50 µl volumes bilaterally by intranasal instillation. At daily intervals after challenge, nasal washes were performed using 0.5 ml PBS with 2% (w/v) BSA per mouse. The presence of shed influenza virus in nasal wash samples was assessed immediately after sampling. Nasal wash samples in serum-free Eagle's minimal essential medium were plated on TPCK-trypsin treated confluent monolayers of MDCK cells in 96-well tissue culture plates. After incubation for 3 days at 35° C., the presence of virus in each well was determined by incubation of 50 µl supernatant with an equal volume of 0±7% (v/v) turkey red blood cells. Virus positive sample produced visible haemagglutination (agglutination spot clearly visible).

Sera ELISA

Sera obtained form sample bleeds were diluted in PBS and kept at −20° C. until assayed by the enzyme-linked immunoadsorbent assay (ELISA). Certified binding chemistry 96-well plates were coated overnight with 50 µl/well of Influenza HA-PR8 antigen (20 µg/ml) in PBS. Incubate overnight at 4° C. After overnight incubation wells were washed four times with PBS/Tween 20™ (PBST) then wells were coated with 200 µl of 2% (w/v) BSA in PBS. After 2 h at 37° C., the blocking solution was removed and wells were washed four times with PBST and overlaid with dilutions of the different experimental serum (individual animal sample bleeds) starting at dilution ¹⁄₁₀₀ (50 µl sample/well). Following 1 h incubation at 37° C., plates were washed four times with PBST and overlaid 50 µl/well of rabbit anti-mouse Ig-HRP conjugated sera (Dako). After 1 h at 37° C., plates were washed four times with PBST and overlaid with 50 µl/well of substrate solution 3,3',5,5'tetramethylbenzidine (TMB, Pierce). The reaction was stopped by adding 50 µl/well of stopping solution (2M sulphuric acid) and the absorbance, of each well at 450 nm was determined.

Results

The liposomal physical characteristics (% product (DNA and/or protein) entrapment, particle size and surface potential (Zeta)) are summarized in Table 8.

TABLE 8

| | Dose 1 | Dose 2 | Dose 1 | | Dose 2 | |
|---|---|---|---|---|---|---|
| | % entrapment | % entrapment | Size | Zeta | Size | Zeta |
| Group | DNA Protein | DNA Protein | nm | mV | nm | mV |
| 3.1 | 80.0  78.9 | 89.3  91.1 | 913 | ND | 820 | 43 |
| 3.2 | 85.6  81.5 | 92.2  91.0 | 821 | ND | 906 | 43 |

ND = not determined.

The antibody responses (Sera Elisa) are expressed as the mean (n=5 animals/group) OD signal±SEM at the $Log_{10}$ serum dilution assayed. Results are expressed in FIG. 7, which shows the response after one dose and FIG. 8 which shows the results after two doses.

The live virus challenge results are presented in Table 9, as the percentage of animals (n=15 challenged)/group which presented detectable virus in nasal wash samples obtained.

TABLE 9

| Group | Day 1 | Day 2 | Day 3 | Day 4 | Day 5 |
|---|---|---|---|---|---|
| 3.1 | 0 | 0 | 3.3 | 30 | 3.6 |
| 3.2 | 6.7 | 6.7 | 53.3 | 50 | 3.3 |
| 3.3 | 0 | 35.7 | 39.3 | 60.7 | 50 |
| 3.4 | 0 | 66.7 | 93.3 | 100 | 82.1 |

Discussion

Figure 7:
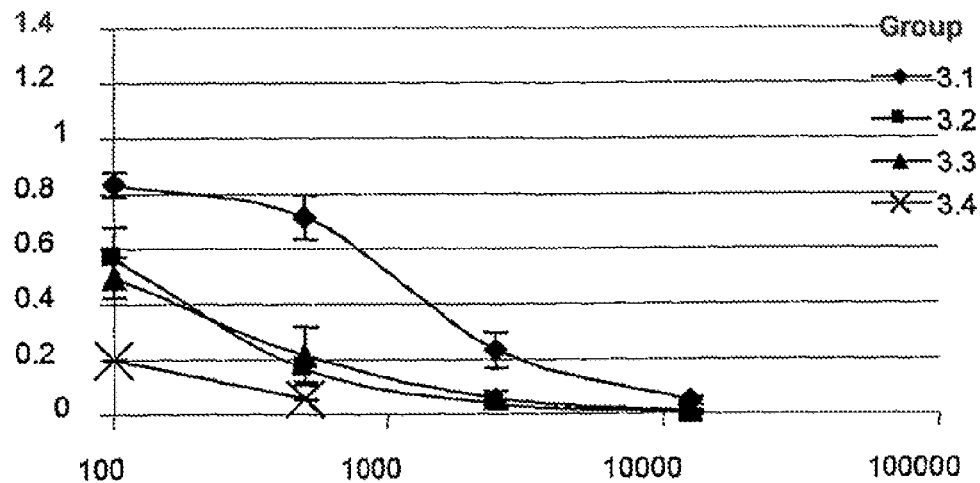
FIG. 7 shows the antibody responses (Sera ELISA) results post one dose.
Figure 8:
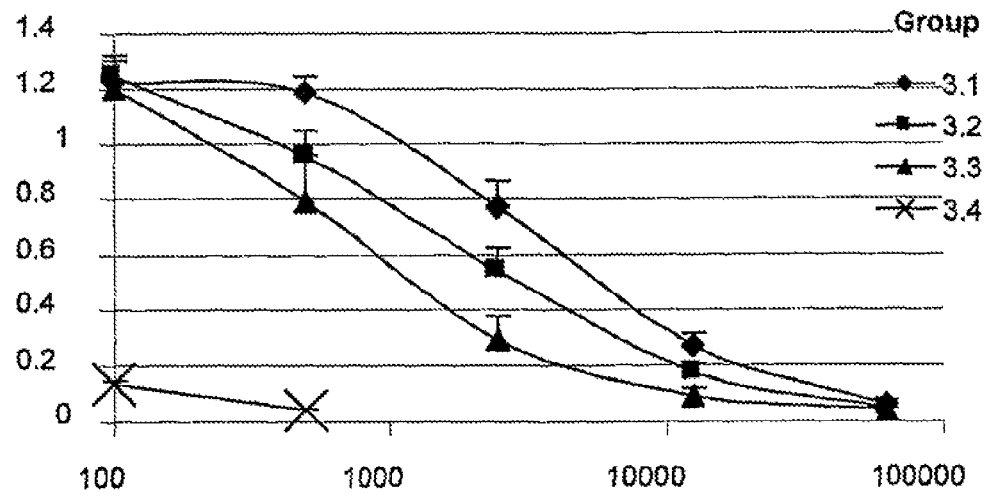
FIG. 8 shows the antibody responses (Sera ELISA) post second dose.

The immune response generated following immunization with formulations (Table 7) was assessed by measurement of anti influenza (A/PR8 strain specific) response. Results are illustrated in FIGS. 7 and 8. Group (Formulation) 3.1 which consisted of both HA DNA and protein co-delivered in the same liposomal formulation produces a greater response than all the other groups (formulations) at each sera sample bleed tested (day 21 and day 42 (day 14 following the second dose)). The response for this co-delivered formulation group (3.1.1) is greater in terms of magnitude of both OD450 nm sera dilution an titre (endpoint read OD 0.3 units).

The response to the payload components, HA DNA and protein admixed (group 3.3), consistently generates a weaker immune response than the same payload components co-delivered (group 3.1). Indeed, using the same DNA paylaod (at 10 μg DNA dose) with a reduced protein payload (0.5 μg protein dose) in the same liposomal vehicle (group 3.2), produces an equivalent serum Ig immune response to HA DNA and protein admixed with 3-fold greater protein component payload (group 3.3). Group 3.4 failed to produce any specific anti Ig influenza response, however this group received no immunogenic components (PBS only) thus this result is as expected.

The live virus challenge results serve to indicate if the immune response induced in the mice in response to immunisation with the formulations is adequate to protect the animals from virus infection. Group 3.4 services as a negative control, as these are essentially 'naïve' animals they reflect the normal profile of the virus infection following challenge. In the group (3.4) all animals are infected with virus by day 4, with an average % (over 5 days) of 68% (sem 18%) animals-infected. Group 5.3 which consisted of the payload components, HA DNA and protein admixed, non liposomally co-delivered whilst inducing an anti influenza response FIG. 7 failed to demonstrate a significant (relative to group 3.4) reduction in the % of animals are infected with virus with an average % (over 5 days) of 37% (sem 10% animals infected. Group (formulation) 3.1 which consisted of both HA DNA and protein co delivered in the same liposomal formulation produced a greater response antibody response FIGS. 7 and 8 than all the other groups (formulations) and demonstrates a significant (relative to group 3.4) ($p<0.05$) reduction in the % of animals are infected with virus with an average % (over 5 days) of only 7% (sem 6% animals infected.

In summary we have found that the present invention is highly effective for generating an immune response, which is capable of protecting an individual from infection with an infectious organism when administered to a subject. The response involves an antibody response. The improvement exhibited by the present invention involves composition of liposome forming materials delivering a payload of nucleic acid operatively encoding an antigenic protein and an co-delivered protein, wherein the co-delivered protein shares epitopes with the antigenic protein.

Example 4

Multivalent Influenza Vaccine

Materials and Methods
Lipids
Egg phosphatidylcholine (PC), Dioleoyl phosphatidylethanolamine (DOPE) and 1,2-dioleoyl-3-(trimethylammonium) propane (DOTAP) were purchased from Sigma Chemical Co., UK. All lipids were stored (−20° C.) dissolved in chloroform purged with nitrogen.
DNA
The plasmids PI17/HA-Sichuan and PI.18/PR8-HA were provided by Dr. J. Robertson (NIBSC, UK)) and contain the full length HA sequence from, respectively, Influenza A/Sichuan/2/87 and Influenza A/Puerto Rico/8/34. Plasmids for dosing were commercially produced by Aldevron (Fargo, USA) and contained <100 Endotoxin Unit (EU)/mg of DNA with no residual protein detectable.
Proteins
Influenza A/Sichuan/2/87 and Influenza A/Puerto Rico/8/34 whole inactivated virus protein (sucrose gradient purified, major protein HA, ref antigen HA) were obtained from NIBSC, UK.
Preparation of Liposome Composition Briefly, small unilamella vesicles (SUV) were prepared from egg phosphatidylcholine (PC) and dioleoyl phosphatidylcholine (DOPE) and 1,2-dioleoyloxy-3-(trimethyl-ammonium) propane (DOTAP) (4:2:1 molar ratio) by sonication were mixed with either pI17/HA-Sichuan DNA and Influenza A/Sichuan/2/87 virus protein or PL18/PR8-HA DNA and Influenza A/Puerto Rico/8/34 virus protein (see) Table 10. Formulations were prepared in duplicate, one vial for dosing and one vial for % entrapment calculations based radio labeled tracer (HA: DNA and protein) added to entrapped materials and freeze-dried overnight as described in Gregoriadis, G., Saffie, R. and Hart, S. L., "High yield incorporation of plasmid DNA within liposome: effect on DNA integrity and transfection efficiency," *J Drug Targeting* (1996) 3(6):467-475 and in Kirby, C., Gregoriadis, G., "Dehydration-rehydration vesicles (DRV): A new method for high yield drug entrapment in liposomes," *Biotechnology* (1994) 2:979-984. Following rehydration under controlled conditions, the generated dehydrated-rehydrated vesicles (DRV liposomes) were washed by centrifugation to remove non-incorporated DNA. The washed pellets were resuspended in PBS to the required dose volume. DNA and/or protein incorporation into was estimated on the basis of $^{35}S$ (for DNA) and $^{125}I$ (for protein) radioactivity recovered in the suspended pellets. Liposomes were subjected to microelectrophoresis and photon correlation spectroscopy (PCS) at 25° C. in a Malvern Zetasizer 3000 to determine their zeta potential (ZP) and z-average diameter respectively.
Animal Procedures Female Balb/c mice 6-12 weeks old (Harlan, UK) were immunised by subcutaneous injection administered in 0.2 ml dose volume. Final dose quantities are summarised in Table 10. Mice received one dose on day 0, with sample bleeds collected from the tail vein at days 14 and 28. The liposomal composition for group 4.3 was an admixture of the compositions for groups 4.1 and 4.2 mixed immediately before administration.

TABLE 10

| Group (formulation) | Dose Quantity Total/animal | | | | |
|---|---|---|---|---|---|
| | pI17/HA-Sichuan DNA | A/Sichuan/2/87 virus protein | pL18/PR8-HA DNA | A/PuertoRico/8/34 virus protection | Lipid mg |
| 4.1 | 10 μg | 1.5 μg | — | — | 2.1 |
| 4.2 | — | — | 10 μg | 1.5 μg | 2.1 |
| 4.3 | 10 μg | 1.5 μg | 10 μg | 1.5 μg | 4.2 |
| 4.4 | — | — | — | — | nil (PBS) |

Sera ELISA

Sera obtained from sample bleeds were diluted in PBS and kept at −20° C. until assayed by the enzyme-linked immunoadsorbent assay (ELISA). Two different protocols were used depending of the protein substrate being detected.

For HA-PR8, certified binding chemistry 96-well plates were coated with 50 μl/well of Influenza HA-PR8 antigen (20 μg/ml) in PBS. After overnight incubation at 4° C. wells were washed four times with PBS/Tween 20™ (PBST) then wells were coated with 200 μl of 2% (w/v) BSA in PBS. After 1 h at 37° C., the blocking solution was removed and wells were washed four times with PBST and overlaid with 50 μl/well of dilutions of the different experimental serum (individual animal sample bleeds) starting at dilution 1/100. Following 1 h incubation at 37° C., plates were washed four times with PBST and overlaid 50 μl/well of rabbit anti-mouse Ig-HRP conjugated sera (Dako). After 1 h at 37° C., plates were washed four times with PBST and overlaid with 50 μl/well of substrate solution 3,3',5,5'tetramethylbenzidine (TMB, Pierce). The reaction was stopped by adding 50 μl/well of stopping solution (2M sulphuric acid) and the absorbance of each well at 450 nm was determined.

For HA-Sichuan, certified binding chemistry 96-well plates were coated with 50 μl/well of a 1/2000 dilution of anti-HA Sichuan sheep serum (NIBSC standard reagent) in 0.1M Carbonate buffer (pH 9.5). After overnight incubation at 4° C. wells were washed four times with PBS/Tween 20™ (PBST) then wells were coated with 200 μl of 2% (w/v) BSA in PBS. After 1 h at 37° C., the blocking solution was removed and wells were washed four times with PBST and overlaid with 50 μl/well of HA-Sichuan antigen (5 μg/ml) in PBS. After 1 h at 37° C., the antigen solution was removed and wells were washed four times with PBST and overlaid with 50 μl/well of dilutions of the different experimental serum (individual animal sample bleeds) starting at dilution 1/100. Following 1 h incubation at 37° C., plates were washed four times with PBST and overlaid 50 μl/well of rabbit anti-mouse Ig-HRP conjugated sera (Dako). After 1 h at 37° C., plates were washed four times with PBST and overlaid with 50 μl/well of substrate solution 3,3',5,5'tetramethylbenzidine (TMB, Pierce). The reaction was stopped by adding 50 μl/well of stopping solution (2M sulphuric acid) and the absorbance of each well at 450 nm was determined.

Results

The liposomal physical characteristics (% product (DNA and/or protein) entrapment, particle size and surface potential (Zeta)) are summarized in Table 11.

TABLE 11

| Group | % entrapment DNA | % entrapment Protein | Size nm | Zeta mV |
|---|---|---|---|---|
| 4.2 | 96.7 | 92.2 | 676 | 48.4 |
| 4.1 | 93.9 | 87.4 | 816 | 42.7 |

The antibody responses (Sera ELISA) are expressed as the mean (n=5 animals/group) OD signal±SEM at the $\text{Log}_{10}$ serum dilution assayed. Results are expressed in FIGS. 9a-d.

Discussion

The immune response generated following immunization with formulations (Table 10) was assessed by measurement of anti influenza HA-PR8 and HA-Sichuan strain specific antibody responses. Results are illustrated in FIGS. 9a-d.

At day 14, a clear antibody response to the Influenza antigens was detected in all experimental groups with the exception of formulation 2 (PBS). Immunization with formulation 4.3, consisting of HA DNA and proteins for both Influenza Sichuan and Influenza Puerto Rico 8, induced equivalent antibody titers, within standard error of the mean (SEM), to each of the strains as those induced following immunization with formulation 4.1 (Influenza Sichuan DNA and protein) or formulation 4.2 (Influenza Puerto Rico 8).

At day 28, there was marked increase in the antibody response to the Influenza antigen compared to day 14. In addition, immunization with formulation 3, consisting of HA DNA and proteins for both Influenza Sichuan and Influenza Puerto Rico 8, again induced equivalent antibody titers, within SEM, to the Influenza Sichuan strain to those induced following immunization with formulation 4.1 (Influenza Sichuan DNA and protein). In contrast, immunization with formulation 4.3, consisting of HA DNA and proteins for both Influenza Sichuan and Influenza Puerto Rico 8, induced antibody titers to the Influenza Puerto Rico 8 strain below those induced following immunization with formulation 4.2 (Influenza Puerto Rico 8) at two dilution points tested.

In summary, we have found that the present invention, when applied to the delivery of multivalent (e.g., multi-strain), is highly effective in inducing antibody responses to the different strains present in the formulation. This antibody response develops quickly (antigen specific antibody titers are >1000 only 14 days after a single immunization) and it can be of the same level as that induced by the present invention when delivering only DNA and protein components of one single strain (e.g., monovalent formulations). Even in occasions when immunization with a multivalent formulation may induce a lower antibody response to one of the strains compared to that induced by the equivalent monovalent formulation, the level of this response is again high (>1000 titer) and increases with time. Therefore, the improvement caused by the present invention, and exemplified in this experiment, is the ability to induce a clear antibody response to several different antigenic strains following a single immunization with a formulation containing DNA and protein antigens from all these strains.

Example 5

Entrapment Levels of DNA and Protein and Liposome Sizes

The general method of liposome formulation noted in Example 1 was used to entrap hepatitis B surface antigen and plasmid DNA encoding that antigen, at various levels of protein, shown in Table 12. The percentage entrapment values are shown in Table 12 and Table 13 shows the average size and zeta potential of the liposomes.

TABLE 12

Entrapment of HbsAg protein and/or DNA encoding HbsAg into liposomes

| | DNA | Protein | Lipid PC:DOPE:DOTAP | % Entrapment DNA | % Entrapment Protein |
|---|---|---|---|---|---|
| 5.1 | 62.0 μg | 17.68 μg | 9.07:4.53:2.27 μM 6.96 + 3.37 + 1.59 mg (total lipid 11.92 mg) | 98.9 | 64.4 |
| 5.2 | 62.0 μg | 3.536 μg | 9.07:4.53:2.27 μM 6.96 + 3.37 + 1.59 mg (total lipid 11.92 mg) | 100 | 76.4 |
| 5.3 | 62.0 μg | 0.697 μg | 9.07:4.53:2.27 μM 6.96 + 3.37 + 1.59 mg (total lipid 11.92 mg) | 100 | 66.2 |
| 5.4 | — | 17.68 μg | 9.07:4.53:2.27 μM 6.96 + 3.37 + 1.59 mg (total lipid 11.92 mg) | — | 74.9 |

TABLE 12-continued

Entrapment of HbsAg protein and/or DNA encoding HbsAg into liposomes

| | DNA | Protein | Lipid PC:DOPE:DOTAP | % Entrapment DNA | Protein |
|---|---|---|---|---|---|
| 5.5 | — | 3.536 μg | 9.07:4.53:2.27 μM<br>6.96 + 3.37 + 1.59 mg<br>(total lipid 11.92 mg) | — | 80.4 |
| 5.6 | — | 1.23 μg | 9.07:4.53:2.27 μM<br>6.96 + 3.37 + 1.59 mg<br>(total lipid 11.92 mg) | — | 93.8 |

Table 12 shows that entrapment of DNA was highly efficient, whereas that of the HbsAg protein was moderately less so. The presence of plasmid DNA had a modest negative effect on the efficiency of entrapment of protein. However, when protein and DNA were entrapped together, there was no negative effect on the entrapment of DNA. These data demonstrate that the efficient co-entrapment of DNA and protein in these liposomal formulations is not unique to the influenza-A hemagglutinin, or unique to any one plasmid. It is likely that if efficient entrapment of DNA and protein is a general property of those liposomal compositions, applicable to virtually any combination of plasmid DNA and protein antigen.

TABLE 13

Z Average size (nm) & zeta potential (mV) for liposomes used in HbsAG formulations

| Formulation | Size nm | Zeta potential mV |
|---|---|---|
| 5.1 | 547 | +45 |
| 5.2 | 710 | +37 |
| 5.3 | 704 | +39 |
| 5.4 | 666 | +41 |
| 5.5 | 694 | +33 |
| 5.6 | 639 | −10 |

It is evident from these data on liposomal formulations of hepatitis-B surface antigen and various plasmid DNAs, that the size range is appropriate to uptake by classical antigen presenting cells such as macrophages and dendritic cells. Uptake of materials from these liposomes by B-cells is likely to require some degree of fragmentation or degradation in vivo or evolve liposomes of smaller size within the heterogeneous population of liposome formulation.

Example 6

Non-Phospholipidic Formulations

Vehicle Materials

Materials 1-monopalmitoyl-rac-glycerol (C16:0) (Monopal), cholesterol (CHOL) and 3 beta-[N—(N',N'-dimethyl-amino-ethane)carbamoyl] cholesterol (DC-Chol) were purchased from Sigma Chemical Co., UK. All materials were stored (−20° C.) dissolved in chloroform, purged with nitrogen.

DNA

Plasmid pCI-OVA (ref DNA OVA) (a kind gift of Dr. T. Nagata, Hamamatsu University School of Medicine, Japan) contains the chicken egg albumin protein (ovalbumin, OVA) (Yoshida A, Nagata T, Uchijima M, Higashi T, Koide Y, "Advantage of gene gun-mediated over intramuscular inoculation of plasmid DNA vaccine in reproducible induction of specific immune response." *Vaccine* (2000) 18:1725-1729) cDNA cloned at the EcoRI site of the pCI plasmid (Promega, Madison, Wis.) downstream from the CMV enhancer/promoter region. Plasmid p1.18/PR8-HA (ref DNA HA) was provided by Dr. J. Robertson (NIBSC, UK) containing the full length HA from influenza A/Puerto Rico/8/34. Plasmid for dosing was commercially produced by Aldevron (Fargo, USA) and contained <100 Endotoxin Unit (EU)/mg of DNA with no residual protein detectable.

Proteins

Influenza A/Puerto Rico/8/34 whole inactivated virus protein (sucrose gradient purified, major protein HA, ref antigen HA) was obtained from the NIBSC, UK.

Preparation of Compositions

Delivery system vehicles were prepared from Monopal and Chol and DC-Chol (4:2:1 molar ratio) by film drying under vacuum the resulting film was hydrated with water by shaking for 1 h at 60° C., after cooling to RT, they were mixed with DNA (ref DNA HA or DNA OVA) and/or protein (ref antigen HA) see Table 14. Formulations were prepared in quadruplicate, two vials for dosing (prime and boost) and two vial for % entrapment calculations based radio labeled tracer (DNA and protein) added to entrapped materials and freeze-dried overnight as described in Gregoriadis, G., Saffie, R. and Hart, S. L., "High yield incorporation of plasmid DNA with liposome: effect on DNA integrity and transfection efficiency," *J Drug Targeting* (1996) 3(6):467-475, and in Kirby, C., Gregoriadis, G., "Dehydration-rehydration vesicles (DRV): A new method for high yield drug entrapment in liposomes," *Biotechnology* (1994) 2:979-984. Following rehydration under controlled conditions, the generated dehydrated-rehydrated vesicles (DRV) were washed by centrifugation to remove non-incorporated DNA. The washed pellets were resuspended in PBS to the required dose volume. DNA and/or protein incorporation into was estimated on the basis of $^{35}S$ (for DNA) and $^{125}I$ (for protein) radioactivity recovered in the suspended pellets. Vehicles were subjected to microelectrophoresis and using laser diffraction at 25° C. in a Malvern Zetasizer 3000 and Malvern Mastersizer to determine their zeta potential (ZP) and z-average diameter respectively.

Animal Procedures

Female Balb/c mice 6-12 weeks old (Harlan, UK) were immunised by subcutaneous injection administered in 0.2 ml dose volume. Final dose quantities are summarised in Table 14. Mice received two doses on days 0 and 28, with sample bleeds collected from the tail vein at day 21 (post 1 dose) and 42 (post 2 doses) with respect to the first injection.

TABLE 14

| Group | Dose Quantity Total/animal | | |
|---|---|---|---|
| (formulation) | DNA μg | Protein (HA) μg | Vehicle mg |
| 6.1 | 10 (HA) | 1.5 | 5.7 |
| 6.2 | 10 (OVA) | 1.5 | 5.7 |
| 6.3 | 10 (HA) | 1.5 | 11.4 |
| 6.4 | nil | 1.5 | 5.7 |
| 6.5 | 10 | nil | 5.7 |
| 6.6 | nil | 1.5 | nil (PBS) |

In the composition of groups 6.1 and 6.2 the DNA and protein were coentrapped. In the composition of groups 6.3 the DNA and protein were separately entrapped and admixed, i.e., this was an admixture of 6.4 and 6.5. In group 6.6 the protein was not entrapped.

Sera ELISA

Sera obtained form sample bleeds were diluted in PBS and kept at −20° C. until assayed by the enzyme-linked immunoadsorbent assay (ELISA). Certified binding chemistry 96-well plates were coated overnight with 50 µl/well of Influenza HA-PR8 antigen (20 µg/ml) in PBS. Incubate overnight at 4° C. After overnight incubation wells were washed four times with PBS/Tween 2™ (PBST) then wells were coated with 200 µl of 2% (w/v) BSA in PBS. After 2 h at 37° C., the blocking solution was removed and wells were washed four times with PBST and overlaid with dilutions of the different experimental serum (individual animal sample bleeds) starting at dilution 1/100 (50 µl sample/well). Following 1 h incubation at 37° C., plates were washed four times with PBST and overlaid 50 µl/well of rabbit anti-mouse Ig-HRP conjugated sera (Dako). After 1 h at 37° C., plates were washed four times with PBST and overlaid with 50 µl/well of substrate solution 3,3',5,5'tetramethyl-benzidine (TMB, Pierce). The reaction was stopped by adding 50 µl/well of stopping solution (2M sulphuric acid) and the absorbance of each well at 450 nm was determined.

Results

The vehicle physical characteristics (% product (DNA and/or protein) entrapment, particle size and surface potential (Zeta)) are summarized in Table 15.

TABLE 15

| Group | Dose 1 % entrapment DNA | Dose 1 % entrapment Protein | Dose 2 % entrapment DNA | Dose 2 % entrapment Protein | Dose 1 Size nm | Dose 1 Zeta mV | Dose 2 Size nm | Dose 2 Zeta mV |
|---|---|---|---|---|---|---|---|---|
| 6.1 | 96.7 | 89.7 | 98.3 | 88.0 | 4140 | 23 | 3770 | ND |
| 6.2 | 94.6 | 90.2 | 79.4 | 82.8 | 4620 | 23.9 | 2950 | ND |
| 6.4 | ND | 86.9 | ND | 92.8 | 4550 | 23.6 | 4060 | ND |
| 6.5 | 97.2 | ND | 97.2 | ND | 4150 | 24.9 | 3580 | ND |

ND = not determined.

The individual animal (n=5/group) antibody responses (Sera ELISA) are expressed as the reciprocal serum dilution required for OD to reach a reading of 0.270 (end point dilution, ~x2 normal mouse sera OD at 1/100 dilution assayed). Results are expressed in FIG. 10.

Discussion

Figure 10:
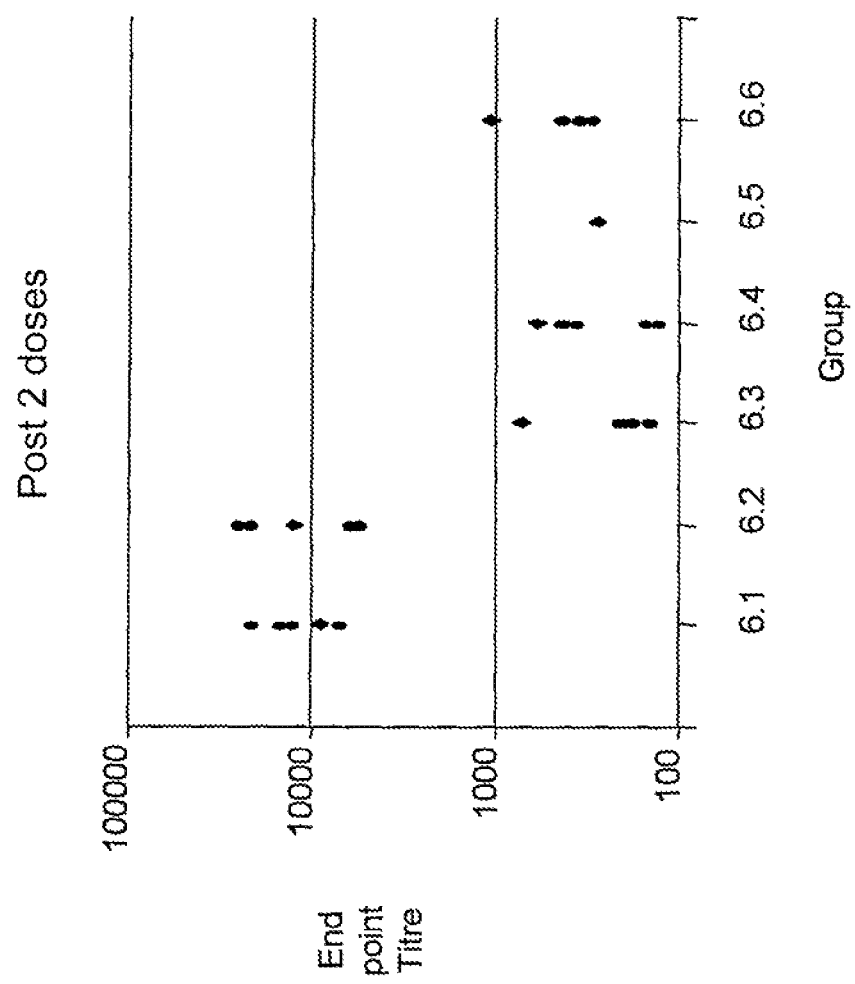
FIG. 10 shows the immune response generated following immunization with formulations (Table 14) assessed by measurement of anti influenza (A/PR8 strain specific) response.

The immune response generated following immunization with formulations (Table 14) was assessed by measurement of anti influenza (A/PR8 strain specific) response. Results are illustrated in FIG. 10. Group (formulation) 6.1 which consisted of both HA DNA and protein co-delivered in the same delivery vehicle produces a greater response than all the other groups except group 6.2.

The results indicate that: delivery of HA protein offers no advantage over protein alone (Group 6.4 vs Group 6.6), delivery of HA DNA alone produces no significant antibody response (Group 6.5) indeed 4 out of 5 animals fail to induce an response greater than the limit of detection of the assay (1/100) dilution sera), admix delivery of HA DNA and protein in separate vehicles (Group 6.3) offers no advantage over protein alone or vehicle delivered protein (Group 6.6 and 6.4 respectively) and co-delivery of HA Protein with a DNA (HA or OVA, Groups 6.1 and 6.2) component generates a significantly higher anti HA response than, admix delivered material or materials delivered alone (Groups 6.3, 6.4, 6.5 and 6.6 respectively).

In the context of this invention the last observation is applicable to both the "cognate" and "irrelevant" DNA component. The immune system response assayed are restricted to antibody responses and cellular mediated immune response (T helper, CTL, etc) have not examined. Thus equivalence in immune responses to "cognate" and "irrelevant" DNA groups (Group 6.1 and 6.2) cannot be concluded. Indeed, HA DNA alone immunisation (Plasmid DNA encoding influenza virus haemagglutinin induces Th1 cells and protection against respirator infection despite its limited ability to generate antibody response. Johnson P A, Conway M A, Daly J. Nicolson C, Robertson J, Mills K H., *J Gen Virol.* (2000) July; 81 (Pt 7):1737-1745, has been found to provide protection from influenza challenge in the absence of antibody responses thus based cellular mediated immune response alone. As group 6.1 "cognate" co-delivery posses HA DNA as a active component of the formulation and group 6.2 "irrelevant" does not contain HA DNA as a active component of the formulation, it does not seem unreasonable to suggest that group 6.1 may induce an additional cellular mediated immune response which has not been measured.

In summary, we have found that the present invention is highly effective for generating an immune response. The response involves an antibody response. The improvement exhibited by the present invention composition of a delivery vehicle without phospholipid components delivering a payload of nucleic acid operatively encoding an antigenic protein and a co-delivered protein.

The invention claimed is:

1. A composition for generating an immune response in a mammal comprising:
   liposomes that are associated with at least two different nucleic acids and at least a first assistor protein;
   wherein at least one of the nucleic acids operatively encodes an antigenic protein or portion thereof which shares at least one epitope with the first assistor protein;
   wherein the liposomes have an average diameter in the range of 100 nm to 2,000 nm;
   wherein the nucleic acids encoding said antigenic proteins and the assistor proteins are associated with the same liposomes;
   wherein the nucleic acid is entrapped in the intravesicular space of the liposomes; and, the assistor protein is displayed on the surface of the same liposome as the nucleic acids,
   whereby the nucleic acids and assistor proteins will be co-delivered by the liposomes to a cell.

2. The composition of claim 1, wherein a single liposome contains the two different nucleic acids, and the liposome is further associated with a second assistor protein.

3. The composition of claim 2, wherein one of the two different nucleic acids operatively encodes an antigenic protein or portion thereof which shares at least one epitope with the first assistor protein, and the other nucleic acid operatively encodes an antigenic protein or portion thereof which shares at least one epitope with the second assistor protein.

4. The composition of claim 1, wherein both of the two different nucleic acids operatively encode an antigenic protein or portion thereof which share at least one epitope with the first assistor protein.

5. The composition of claim 1, wherein the liposomes include at least one cationically charged component such that the liposomes have an overall positive charge.

6. The composition of claim 5, wherein the cationic component is 1, 2-bis (oleoyloxy)-3-(trimethylammonio) propane (DOTAP), 1, 2-bis (hexadecyloxy)-3-trimethylaminopropane (BisHOP), β[1-(2,3-dioleyloxy)propyl]-N,N,N- triethylammoniumchloride (DOTMA) or 3β-(N,N-dimethylaminoethane) carbamyl-cholesterol (DC-CH0L).

7. The composition of claim 1, wherein the antigenic protein or portion encoded by the nucleic acid encoding the epitope is that of an infectious agent.

8. The composition of claim 7, wherein the infectious agent is a virus.

9. The composition of claim 1, wherein the liposomes have an average diameter in the range of 100 nm to 400 nm.

10. The composition of claim 1, wherein the antigenic protein or portion encoded by the nucleic acid encoding the epitope shared by the assistor protein is that of a bacterium.

11. The composition of claim 1, wherein the antigenic protein or portion encoded by the nucleic acid encoding the epitope shared by the assistor protein is that of a host protein selectively expressed on cancerous cells or tissue.

12. The composition of claim 1, wherein the nucleic acid is DNA.

13. A composition for generating an immune response in a mammal comprising:
    liposomes that are associated with a nucleic acid and at least two assistor proteins;
    wherein the nucleic acid operatively encodes an antigenic fusion protein which shares at least one epitope with each of the assistor proteins;
    wherein the liposomes have an average diameter in the range of 100 nm to 2,000 nm;
    wherein the nucleic acid encoding said antigenic fusion protein and said at least two assistor proteins are associated with the same liposomes;
    wherein the nucleic acid is entrapped in the intravesicular space of the liposomes; and, the at least two assistor proteins are displayed on the surface of the same liposome as the nucleic acid, whereby the nucleic acid and the at least two assistor proteins will be co-delivered by the liposomes to a cell.

14. The composition of claim 13, wherein the liposomes include at least one cationically charged component such that the liposomes have an overall positive charge.

15. The composition of claim 14, wherein the cationic component is 1, 2-bis (oleoyloxy)-3-(trimethylammonio) propane (DOTAP), 1, 2-bis (hexadecyloxy)-3-trimethylaminopropane (BisHOP), β[1-(2,3-dioleyloxy)propyl]-N,N,N-triethylammoniumchloride (DOTMA) or 3β-(N,N-dimethylaminoethane) carbamyl-cholesterol (DC-CHOL).

16. The composition of claim 13, wherein the nucleic acid is DNA.

17. The composition of claim 13, wherein the liposomes have an average diameter in the range of 100 nm to 400 nm.

18. The composition of claim 13, wherein the antigenic protein or portion encoded by the nucleic acid encoding the epitope shared by the at least two assistor proteins is that of an infectious agent.

19. The composition of claim 18, wherein the infectious agent is a virus.

20. The composition of claim 13, wherein the antigenic protein or portion encoded by the nucleic acid encoding the epitope shared by the at least two assistor proteins is that of a bacterium.

21. The composition of claim 13, wherein the antigenic protein or portion thereof encoded by the nucleic acid encoding the epitope shared by the at least two assistor proteins is that of a host protein selectively expressed on cancerous cells or tissue.

22. The composition of claim 13, wherein the antigenic protein or portion encoded by the nucleic acid encoding the epitope shared by the at least two assistor proteins is that of a host protein or peptide requiring neutralisation or elimination.

* * * * *